US006361807B1

(12) United States Patent
Aviram et al.

(10) Patent No.: US 6,361,807 B1
(45) Date of Patent: Mar. 26, 2002

(54) POMEGRANATE EXTRACTS AND METHODS OF USING THEREOF

(75) Inventors: Michael Aviram, Kiriat-Haim (IL); Leslie Dornfeld, Los Angeles, CA (US)

(73) Assignee: Stewart and Lynda Resnick Revocable Trust, Los Angeles, CA (US)

( * ) Notice: Subject to any disclaimer, the term of this patent is extended or adjusted under 35 U.S.C. 154(b) by 0 days.

(21) Appl. No.: 09/398,655

(22) Filed: Sep. 21, 1999

Related U.S. Application Data

(62) Division of application No. 09/294,307, filed on Apr. 19, 1999.

(51) Int. Cl.$^7$ ............................................... A61K 35/78
(52) U.S. Cl. ...................... 424/744; 424/725; 514/824; 514/944; 514/969
(58) Field of Search ............................ 424/195.1, 725, 424/744; 426/541, 599, 648; 514/824, 944, 969

(56) References Cited

U.S. PATENT DOCUMENTS

| | | |
|---|---|---|
| 5,162,037 A | 11/1992 | Whitson-Fischman |
| 5,411,733 A | 5/1995 | Hozumi et al. |
| 5,624,698 A | 4/1997 | Dake et al. |
| 5,679,351 A | 10/1997 | Walter et al. |
| 5,830,887 A | 11/1998 | Kelly |
| 5,840,308 A | 11/1998 | Jassim et al. |
| 5,850,032 A | 12/1998 | Wann |
| 5,891,440 A | 4/1999 | Lansky |
| 6,030,622 A * | 2/2000 | Shehadeh ................. 424/195.1 |
| 6,060,063 A * | 5/2000 | Lansky ..................... 424/195.1 |

FOREIGN PATENT DOCUMENTS

| | | |
|---|---|---|
| FR | 2178968 * | 3/1972 |
| FR | 2 178 968 | 11/1973 |
| JP | 4124140 * | 4/1992 |
| JP | 5310745 * | 11/1993 |
| JP | 5320037 | 12/1993 |
| JP | 5329063 * | 12/1993 |
| JP | 6110710 * | 4/1997 |
| JP | 9110710 | 4/1997 |
| JP | 10298094 | 11/1998 |
| JP | 410298094 * | 11/1998 |
| JP | 11243911 | 9/1999 |
| RU | 2088119 | 8/1997 |
| SU | 1251851 | 8/1986 |
| SU | 1442167 | 12/1988 |
| SU | 1733448 * | 5/1992 |
| WO | WO 93/23069 | 11/1993 |
| WO | WO 95/22254 | 8/1995 |
| WO | 9624327 * | 8/1996 |
| WO | WO 98/29129 | 7/1998 |
| WO | WO99/66941 | 12/1999 |

OTHER PUBLICATIONS

[Search Report] PCT/US/00/06758; Int'l. Filing Date: Mar. 15, 2000.

[Article] Journal of Ethno–Pharamacology (1999) 66, pp. 11–17, Schubert et al.

[Article] Food Science and Technology International (1998) 4, pp. 99–105, Zafrilla et al.

Glozman et al. Khim.–Farm. Zh. vol. 23 (9), pp. 1111–1115—see English translation, 1989.*

* cited by examiner

*Primary Examiner*—Christopher R. Tate
(74) *Attorney, Agent, or Firm*—Hogan & Hartson, L.L.P.

(57) ABSTRACT

Pomegranate extracts and methods of use thereof are provided. Particularly, an antioxidative composition comprising an extract from pomegranate is provided. A method of reducing lipid peroxidation, aggregation or retention, HDL oxidation in a sample and a method of alleviating atherosclerosis in a patient are also provided.

18 Claims, 14 Drawing Sheets

POMEGRANATE EXTRACTS AND METHODS OF USING THEREOF

This is a division of application Ser. No. 09/294,307 filed Apr. 19, 1999, which application is hereby incorporated by reference in its entirety.

BACKGROUND OF THE INVENTION

1. Area of the Art

The invention relates generally to Pomegranate Extracts and Methods of Using Thereof.

2. Description of the Prior Art

Throughout this application, various references are referred to within parentheses. Disclosures of these publications in their entireties are hereby incorporated by reference into this application to more fully describe the state of the art to which this invention pertains. Full bibliographic citation for these references may be found at the end of this application, preceding the claims.

Major risk factors for atherosclerosis include increased plasma low density lipoprotein (LDL) levels, as well as LDL modifications such as its retention, oxidation and aggregation (1–5). Blood platelets activation also contribute to accelerated atherosclerosis (6–8). Oxidative modification of LDL is thought to play a key role during early atherogenesis. Oxidized LDL (Ox-LDL) is taken up by macrophages at enhanced rates via their scavenger receptors (9), leading to the formation of lipid-laden foam cells, the hallmark of early atherosclerosis (10). Cells of the arterial wall (including endothelial cells, smooth muscle cells and macrophages) can oxidize LDL in vitro in the presence of catalytic amounts of transition metal ions (11–13).

Although increased resistance of LDL to oxidation was observed after treatment with various synthetic pharmaceutical agents (14–17), an effort is made to identify natural food products which can offer antioxidant protection against LDL oxidation. The previous study has demonstrated the beneficial effects against LDL oxidation of dietary supplementation of β-carotene (18, 19), lycopene (20), vitamin E (21) and flavonoids from red wine (22, 23), licorice (24) or olive oil (25).

The pomegranate tree, which is said to have flourished in the Garden of Eden, has been extensively used as a folk medicine in many cultures. In ancient Greek mythology, pomegranates are known as the "fruit of the dead," and in the ancient Hebrew tradition, pomegranates adorned the vestments of the high priest. The Babylonians regarded its seeds as an agent of resurrection, the Persians as conferring invincibility on the battlefield, and for ancient Chinese it symbolized longevity and immortality.

Edible parts of pomegranate fruits (about 50% of total fruit weight) comprise 80% juice and 20% seeds. Fresh juice contains 85% moisture, 10% total sugars, 1.5% pectin, ascorbic acid and polyphenolic flavonoids. Pomegranate seeds are a rich source of lipids, proteins, crude fibers, pectin and sugars.

The dried pomegranate seeds contain the steroidal estrogen estrone (26, 27), the isoflavonic phytoestrogens genistein and daidzein and the phytoestrogenic coumestrol (28). In pomegranate juice, fructose and glucose are present in similar quantities, calcium is 50% of its ash content and the principal amino acids are glutamic and aspartic acid (29, 30). Content of soluble polyphenols in pomegranate juice varied within the limits of 0.2% to 1.0%, depending on variety, and include mainly anthocyanins (such as cyanidin-3-glycoside, cyanidin-3, 3-diglycoside and delphindin-3-glucosid), catechins, ellagic tannins, and gallic and ellagic acids (31).

Constitutes of pomegranate have been studied for their antiviral and antifungal effects. For example, U.S. Pat. No. 5,840,308 (61) describes an antiviral and antifungal composition comprising a mixture of a ferrous salt and an extract of a plant including, inter alia, pomegranate rind. U.S. Pat. No. 5,411,733 (32) describes an antiviral agent containing a crude drug from, inter alia, the root bark and fruit peel of pomegranate.

Prior to the present invention, however, no one has studied the effects of pomegranate extracts on LDL atherogenic modifications, including its retention, oxidation and aggregation. No one has used pomegranate extracts for the purpose of treating or ameliorating atherosclerosis.

SUMMARY OF THE INVENTION

It is an object of the present invention to study any effects of pomegranate extract, particularly the effect as an antioxidant. It is also an object of the present invention to provide methods of using pomegranate extract, for example, as an antioxidant. It is further an object of the present invention to provide a method of preventing or ameliorating atherosclerosis.

Accordingly, one aspect of the present invention provides a composition, the biologically active component of the composition consisting essentially of an extract from pomegranate, and the composition comprising a carrier. The composition may be used as nutritional supplements, pharmaceutical preparations, vitamin supplements, food additives or foods supplements. The composition may be used in a dosage unit as tablets, suspensions, implants, solutions, emulsions, capsules, powders, syrups, liquid compositions, ointments, lotions, creams, pastes, gels, and the like. According to embodiments of the invention, the extract may be an extract of juice or the inner or outer peel of pomegranate, or a mixture thereof.

Another aspect of the present invention provides an antioxidative composition for treating disorders associated with conditions including lipoprotein oxidation, aggregation, retention; macrophage atherogenicity, platelet activation and atheroscleorosis. The biologically active component of the composition consists essentially of an effective amount of an extract from pomegranate. The examples of disorders include arteriosclerotic heart disease and its associated complications, including myocardial infarction; cerebral vascular disease (including cerebral insufficiency or stroke); peripheral vascular disease (including peripheral vascular disease in the aorta and femoral and corotid arteries); abdominal aortic aneurysms; renal artery stenosis; arteriosclerotic disease, disorders associated with transplant complications; disorders associated with post-operative heart valve replacement; disorders associated with the complications of diabetes mellitus; thrombophlebitis; and other disorders associated with increased platelets and increased platelet activation.

A further aspect of the present invention provides a method of ameliorating disorders associated with conditions including lipoprotein oxidation, aggregation, retention; macrophage atherogenicity, platelet activation and atherosclerosis. The method comprises administering to a subject in need thereof a therapeutically effective amount of a composition comprising an extract from pomegranate.

Yet another aspect of the present invention provides a method of ameliorating in a sample conditions including lipoprotein oxidation, aggregation, retention; macrophage atherogenicity and platelet activation. The method comprises a step of contacting the sample with a sufficient amount of an extract from pomegranate.

The invention is defined in its fullest scope in the appended claims and is described below in its preferred embodiments.

DESCRIPTION OF THE FIGURES

The above-mentioned and other features of this invention and the manner of obtaining them will become more apparent, and will be best understood, by reference to the following description, taken in conjunction with the accompanying drawings. These drawings depict only a typical embodiment of the invention and do not therefore limit its scope. They serve to add specificity and detail, in which:

FIG. 1(A) shows the extent of plasma lipid peroxidation measured by the TBARS assay.

FIG. 1(B) shows the extent of plasma lipid peroxidation measured by the lipid peroxides assay.

DETAILED DESCRIPTION OF THE INVENTION

Figure 1:
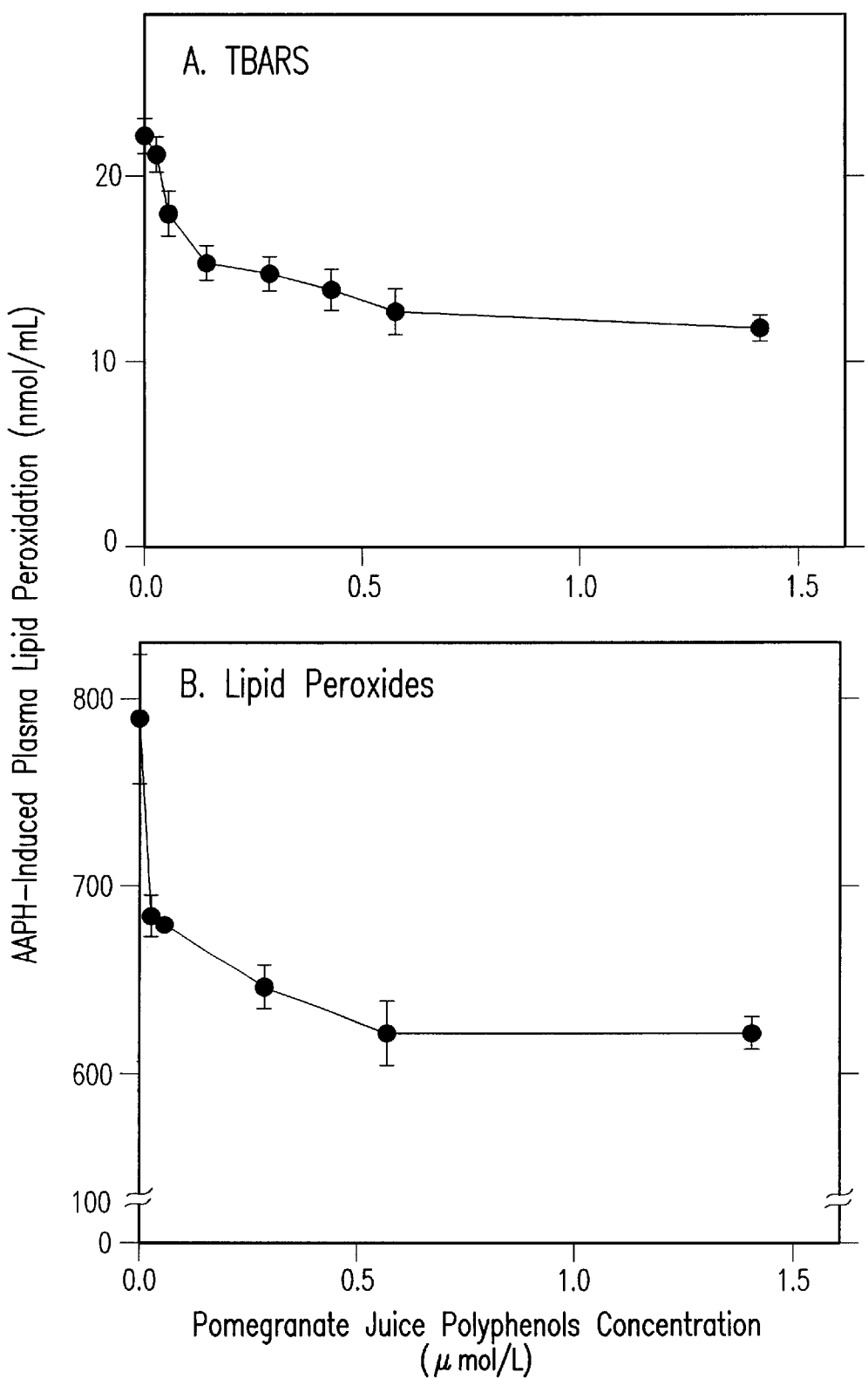
FIG. 1 shows the effect of pomegranate juice on AAPH-induced plasma lipid peroxidation in a juice concentration study.

The present invention demonstrated, for the first time, antiatherogenic properties of pomegranate juice (PJ) or pomegranate extract as related to its inhibitory effect on lipid peroxidation in plasma, in lipoproteins and in macrophages. In addition, pomegranate extract also possesses inhibitory effects on atherogenic modifications of lipoprotein, including its retention, oxidation and aggregation. Furthermore, antiatherogenicity of pomegranate extract could be also related to its ability to attenuate platelet activation, an additional important risk factor for atherosclerosis.

Accordingly, one aspect of the present invention provides a composition, the biologically active component of the composition consisting essentially of an extract from pomegranate. The composition also comprises a carrier.

For the purpose of the present invention, an extract from pomegranate may be an extract from the whole pomegranate or from any constituents of pomegranate. Examples of constituents of pomegranate that may be used to make the extract of the present invention include, but are not limited to, juice, seed, and the inner and outer peel of pomegranate. In one embodiment of the present invention, the extract is juice extract of whole pomegranate. In another embodiment of the present invention, the extract is from the inner or outer peel of pomegranate. In a further embodiment of the present invention, the extract may be a mixture of two or more extracts of the whole pomegranate or any constituents of pomegranate.

Methods of making juice extract of whole pomegranates are commonly known in the art, and need not be repeated here. In general, any methods that may produce pomegranate juice that naturally occurs in pomegranate may be used. For the purpose of the present invention, the juice may be concentrated or diluted from its natural concentration. The juice may also be mixed with extracts of other constituents of pomegranate.

Extracts from constituents of pomegranate, i.e., seed, inner or outer peel, may be made by methods commonly known in the art. For example, the seed, inner or outer peel of pomegranate may be diluted in water and the extract may be made by crushing, squeezing, or extensive vortexing. The insoluble materials of the extract may be separated from the soluble supernatant of the extract. Perferably, the supernatant of the extract is used for the purpose of the present invention, although any oily, lipidic fraction of the extract may also be used. The extract from constituents of pomegranate may be concentrated or diluted, or mixed with each other or with pomegranate juice extract.

The extract of pomegranate of the present invention may be in a liquid or solid form. In accordance with one embodiment of the present invention, a solid form of extract may be made by lyophilizing the liquid extract of the present invention. Other methods that are commonly known in the art may also be used.

Compositions of the present invention may be a variety of kinds, including, but not limited to, nutritional supplements, pharmaceutical preparations, vitamin supplements, food additives or foods supplements. Compositions of the present invention may be in convenient dosage forms, including, but not limited to, tablets, suspensions, implants, solutions, emulsions, capsules, powders, syrups, liquid compositions, ointments, lotions, creams, pastes, gels, or the like.

Compositions of the present invention include a carrier. Depending on the kind of compositions of the present invention, a carrier may be a dietary suitable carrier or a pharmaceutically acceptable carrier, as long as it is compatible with the particular kind of compositions of the present invention. Examples of a dietary suitable carrier include, but are not limited to, dietary suitable excipients, diluents and carriers. Examples of a pharmaceutically acceptable carrier include, but are not limited to, biocompatible vehicles, adjuvants, additives and diluents to achieve a composition usable as a dosage form. As used herein, the terms "pharmaceutically acceptable," "physiologically tolerable" and grammatical variations thereof, as they refer to compositions, carriers, diluents and reagents, are used interchangeably and represent that the materials are capable of administration to or upon a mammal without the production of undesirable physiological effects.

The compositions of the present invention may be used alone or in combination with other biologically active ingredients. A composition of the present invention, alone or in combination with other active ingredients, may be administered to a subject in a single dose or multiple doses over a period of time, generally by oral administration. Various administration patterns will be apparent to those skilled in the art. The dosage ranges for the administration of the compositions of the present invention are those large enough to produce the desired effect. The dosage should not be so large as to cause any adverse side effects, such as unwanted cross-reactions and the like. Generally, the dosage will vary with the age, weight, sex, condition and extent of a condition in a subject, and the intended purpose. The dosage can be determined by one of skill in the art without undue experimentation. The dosage can be adjusted in the event of any counter indications, tolerance, or similar conditions. Those of skill in the art can readily evaluate such factors and, based on this information, determine the particular effective concentration of a composition of the present invention to be used for an intended purpose.

In one embodiment of the present invention, a composition contains the extract of pomegranate in a dosage unit in an amount that contains at least 30 to 3000 $\mu$mols per dosage unit of polyphenols. For the purpose of the present invention, polyphenols are those naturally present in the extract of pomegranate. It should be appreciated that polyphenols are used herein as a measurement for the amount of extract that need to be used in each dosage unit. They are not used herein as an indication that they are the active, or the only active, ingredients of the extract. In fact, it is possible that something else, or the synergy of polyphenols and other components of an extract of the present invention, may be responsible for the activities of the extract.

The term "dosage unit" as used herein refers to physically discrete units suitable as unitary dosages for animals, each unit containing a predetermined quantity of active material calculated to produce the desired therapeutic effect in association with the required diluent, e.g., a carrier or vehicle. The specifications for the unit dose of this invention are dictated by and are directly dependent on (a) the unique characteristics of the active material and (b) the limitations inherent in the art of compounding such active material for therapeutical use in animals.

In accordance with one aspect of the present invention, compositions of the present invention may be used as an antioxidant for treating a disorder associated with a condition including, but not limited to, lipoprotein oxidation, aggregation, retention; macrophage atherogenicity, platelet activation and atheroscleorosis. Therefore, one aspect of the present invention provides an antioxidative composition for preventing or ameliorating disorders associated with a condition selected from a group consisting of lipoprotein oxidation, aggregation, retention; macrophage atherogenicity, platelet activation and atheroscleorosis. The biologically active component of the composition consists essentially of an effective amount of an extract from pomegranate.

The term "an effective amount" as used herein means that the amount of the extract of the present invention contained in an antioxidative composition of the present invention is of sufficient quantity which, upon administration to a subject, may produce some beneficial effect for a subject against a disorder associated with a condition including, but not limited to, lipoprotein oxidation, aggregation, retention; macrophage atherogenicity, platelet activation and atheroscleorosis. Examples of such a disorder include, but are not limited to, arteriosclerotic heart disease and its associated complications including myocardial infarction; cerebral vascular disease (including cerebral insufficiency or stroke); peripheral vascular disease (including peripheral vascular disease in the aorta and femoral and corotid arteries); abdominal aortic aneurysms; renal artery stenosis; arteriosclerotic disease, disorders associated with transplant complications; disorders associated with post-operative heart valve replacement; disorders associated with the complications of diabetes mellitus; thrombophlebitis; and other disorders associated with increased platelets and increased platelet activation.

The antioxidative composition of the present invention may be used alone or in combination with other desirable biological active ingredients. The antioxidative composition of the present invention may also be used in combination with a pharmaceutically acceptable carrier of the present invention.

In accordance with embodiments of the present invention, an antioxidative composition of the present invention may contain the extract of pomegranate in a dosage unit in an amount that contains at least 30 to 3000 $\mu$mols per dosage unit of polyphenols. Preferably, the extract is an extract of juice, seed, inner peel or outer peel of pomegranate. Most preferably, the extract is an extract of inner or outer peel of pomegranate.

The present invention also provides a method of ameliorating disorders associated with a condition including lipoprotein oxidation, aggregation, retention; macrophage atherogenicity, platelet activation and atheroscleorosis. The method comprises administering to a subject in need thereof a therapeutically effective amount of a composition comprising an extract from pomegranate.

The term "therapeutically effective amount" as used herein means that the amount of a composition of the present invention administered is of sufficient quantity to prevent or ameliorate to some beneficial degree a disorder associated with a condition including, but not limited to, lipoprotein oxidation, aggregation, retention; macrophage atherogenicity, platelet activation and atheroscleorosis. The amount must be large enough to produce the desired effect, but not so large as to cause any adverse side effects. Generally, the therapeutically effective amount will vary with the subject's, age, weight, sex, condition, the extent of a condition in the subject, and the potency of the composition, and can be determined by one of skill in the art without undue experimentation. In one embodiment of the present invention, in one dosage unit, a composition may contain an extract of pomegranate in an amount that contains at least 30 to 3000 $\mu$mols of polyphenols per dosage unit. One or more doses may be administered daily, for one or several days or indefinitely. In one embodiment, compositions that contain an extract of pomegranate in an amount that contains at least 300 to 3000 $\mu$mols of polyphenols per dosage unit may be orally administered once daily for a period of at least two weeks. For example, two glasses of pomegranate juice/per day may be consumed by a human for a period of at least two weeks. If the composition is administered by injection, the composition may contain an extract in an amount that contains at least 30 to 600 μmols of polyphenols per dosage unit. The amount in each dosage should be sufficient to result in a serum level of at least 1.5 μmols to 10 μmols of polyphenols. Compositions that contain an extract of pomegranate may be administered to a subject orally or parentally by injection. The compositions are administered in a manner compatible with the dosage formulation and in a therapeutically effective amount. The quantity to be administered and timing of administration depends on the subject to be treated, capacity of the subject's system to utilize the active ingredient, and degree of therapeutic effect desired. Precise amounts of the active ingredient required to be administered depend on the judgement of the practitioner and are peculiar to each individual. However, suitable dosage ranges for systematic application are disclosed herein and depend on the route of administration. Suitable regimens for administration are also variable but are typified by an initial administration followed by repeated doses at intervals by subsequent oral administration, injection or other administration.

The composition of the present invention may also be administered with other active ingredients or a pharmaceutically acceptable carrier. Preparations for oral or parental administration of a composition of the invention include sterile aqueous or non-aqueous solutions. suspensions and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions including saline and buffered media. Parental vehicles include sodium chloride solution, Ringer's dextrose, dextrose and sodium chloride, dextrose and water, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like.

For the purpose of the present invention, a subject may be any subject that is in need of the treatment. Preferably the subject is a mammal. Examples of mammals include, but are not limited to, mice, dogs, cats, hamsters, sheep, goats, cows, pigs, rabbits, humans, and the like. More preferably, the subject is human.

The present invention also provides a method of ameliorating in a sample a condition including lipoprotein oxidation, aggregation, retention; macrophage atherogenicity, and platelet activation. The method comprises a step of contacting the sample with a sufficient amount of an extract from pomegranate.

For the purpose of the present invention, a sample may be a sample from a mammal, particularly from humans. Examples of a sample include, but are not limited to, serum, plasma, urine, lipoproteins such as LDL and HDL, blood, peritoneal macrophages and aortas, and the like. The sample may be contacted with an extract from pomegranate by directly adding the extract to the sample, or by administering the extract to a mammal wherefrom the sample is derived, as described above.

The amount of the extract is sufficiently effective if the condition (such as lipoprotein oxidation, aggregation, retention; macrophage atherogenicity, and platelet activation) may be ameliorated. This amount may vary, depending on the particularity of a sample, the contacting condition, and the invented purpose. One skilled in the art can readily determine the sufficient amount of abstract to be used in view of the disclosure of this invention.

The following examples are intended to illustrate, but not to limit, the scope of the invention. Indeed, those of ordinary skill in the art can readily envision and produce further embodiments, based on the teachings herein, without undue experimentation.

EXAMPLES

Methods

Human studies

Thirteen healthy men, aged 20–35, nonsmokers and under no medication, were included in the study. Subjects were students or laboratory staff from the Technion Faculty of Medicine. They received 50 ml/day of pomegranate juice (1.5 mmoles of total polyphenols/day) for a period of two weeks.

The compliance with the pomegranate juice supplementation in all subjects was satisfactory, as assessed by a daily contact with the subjects. The subject's body mass index (BMI) was 23.0±1.5 and it did not change during the study. All subjects continued with their habitual diet during the study. The study was approved by the Helsinki Committee of the Rambam Medical Center, Israel Ministry of Health (No-912). Blood samples were drawn after 12 hours of fast, before study entry, and after one and two weeks of pomegranate juice consumption.

Mice study

Apolipoprotein E-deficient ($E^\circ$) mice were generously provided by Dr. Jan Breslow, the Rockefeller University, New York. Gene targeting in mouse embryonic stem cells was used to create mice that lack apolipoprotein E (33). Thirty $E^\circ$ mice, aged six weeks, were divided into three groups, 10 mice in each group. The three groups received in their drinking water 0, 6.25 or 12.5 μL of pomegranate juice (equivalent to 0, 0.175 and 0.350 μmoles of total polyphenols) per mouse per day.

Blood was taken at 6, 9 and 14 weeks of age for plasma and LDL analyses. Peritoneal macrophages and aortas were obtained at the end of the study.

Pomegranate processing

Pomegranates were picked by hand, washed, chilled to 32° F. and stored in tanks. Then the fruit was crushed, squeezed and enzymatically treated with pectinase to yield the pomegranate juice and the by-products, which include the inner and outer peels and the seeds. Pectinase hydrolyzes alpha-1,4galacturonide bonds in pectin and thus it improves extraction and filtration, and galacturonidase bonds in pectin and, thus, it improves extraction and filtration, and prevents formation of pectin gels. The juice was filtered, pasteurized, concentrated and stored at −18° C.

Peels and seeds extracts

One gram of inner or outer peels/seeds was diluted in 5 ml of water followed by crushing, squeezing and extensive vortexing. Then the extract was centrifuged to remove any water insoluble materials and the supernatant was used for LDL oxidation analyses (FIG. 4A).

In the seeds extraction, an upper oily, lipidic fraction appeared which was not used in the study of aqueous extracts, but may contain also some active compounds. Therefore, the oily, lipidic fraction may also be used as an extract of the present invention.

As ingredients other than polyphenols may also act as potent antioxidants, the effect of the extract was also studied on the basis of weight (FIG. 4B).

For this purpose, the extracts were lyophilized to remove the aqueous part. Now the pomegranate juice contained about 30-fold more weight material than the peels and thus, when we compared them on the basis of weight, the polyphenols concentration in the pomegranate juice was extremely low and did not act at this low polyphenols concentration as an antioxidant.

In contrast, the peels were active antioxidants, as they contain both polyphenols at high enough concentration to act as antioxidants and additional non-polyphenols antioxidants.

Polyphenols determination

Total polyphenols concentration in pomegranate juice was determined spectrophotometrically with the phosphomolybdic phosphotungstic acid reagents (31).

Plasma lipid peroxidation

Human plasma obtained from a healthy volunteer was diluted (×2) with phosphate buffered saline (PBS). In the in vitro studies, increased concentrations of pomegranate juice polyphenols (0–1.5 $\mu$mol/L) were added to the plasma, whereas in the in vivo studies plasma was obtained from the subjects that participated in the study before and after two weeks of PJ consumption, and from E° mice at 0, 9 and 14 weeks of PJ consumption.

The plasma was incubated in the absence or presence of 100 mmol/L of the free radical generator 2,2'-Azobis 2-amidinopropane hydrochloride (AAPH, Wako Chemical Industries Ltd., Japan) for two hours at 37° C. AAPH is a water-soluble azo compound that thermally decomposes to produce peroxyl radicals at a constant rate. Plasma lipid peroxidation was determined by measuring the amount of generated thiobarbituric acid reactive substances (TBARS) (34) and lipid peroxides (35).

Serum paraoxonase (arylesterase activity)

Arylesterase activity was measured using phenylacetate as the substrate. Initial rates of hydrolysis were determined spectrophotometrically at 270 nm. The assay mixture included 5 $\mu$L of serum, 1.0 mmol/L phenylacetate, and 0.9 mmol/L $CaCl_2$ in 20 mmol/L Tris HCl, pH 8.0. Nonenzymatic hydrolysis of phenylacetate was substracted from the total rate of hydrolysis. The $E_{270}$ for the reaction was 1,3 10 $M^{-1}$ $cm^{-1}$. One unit of arylesterase activity is equal to 1 $\mu$mol of phenylacetate hydrolyze/min/mL (36). In the in vitro study, increasing concentrations of pomegranate juice were incubated with normal serum for 10 minutes prior to the analysis of arylesterase activity.

Total plasma antioxidant status

Total antioxidant status was measured in plasma by a commercially available kit (Randox Laboratories Limited, UK, Cat No. NX 2332) applicable for COBAS MIRA. Plasma was incubated with ABTS (2,2'-Azino-di-[3-ethylbenzthiazoline sulphonate]) and a peroxidase (metmyoglobin) and $H_2O_2$, to produce a radical cation. The resulting product has a relatively stable blue-green color, which is measured at 600 nm. Antioxidants in the added sample cause suppression of this color production to a degree which is proportional to their concentration (37).

Lipoproteins isolation

For the in vitro studies, LDL was isolated from plasma derived from healthy normolipidemic volunteers. For the ex vivo studies, human plasma was collected before study entry (baseline), and after one and two weeks of pomegranate juice administration. In the mice study, LDL was isolated from blood samples drawn from E° mice before and after 9 weeks and 14 weeks of pomegranate juice administration.

Plasma samples were stored at 4° C. for two weeks until all three samples were collected. Then, LDL and HDL were isolated from the plasma samples. No significant differences could be measured in the basal oxidative state (no oxidant added) of the lipoproteins. The lipoproteins (LDL and HDL) were prepared by discontinuous density gradient ultracentrifugation as previously described (38). The lipoproteins were washed at d=1.063 g/mL, dialyzed against 150 mmol/L NaCl, 1 mmol/L $Na_2$ EDTA (pH 7.4) at 4° C. The LDL and HDL fractions were then sterilized by filtration (0.45 $\mu$m), kept under nitrogen in the dark at 4° C. and used within two weeks. The lipoproteins protein concentration was determined with the Folin phenol reagent (39). Prior to oxidation, LDL and HDL were dialyzed against EDTA-free, phosphate buffered saline (PBS) solution at pH7.4, and at 4° C.

Lipoprotein oxidation

LDL or HDL (100 $\mu$g of protein/mL) were incubated with 5 $\mu$mol/L of $CuSO_4$ for three hours at room temperature. Formation of conjugated dienes was continuously monitored by measuring the increase in absorbance at 234 nm (40). Incubations were carried out in the spectrophotometer cuvette (Ultraspec 3000, Pharmacia, LKB, Biochrom Ltd., Cambridge, UK). The initial backround of the samples ranged between 0.1–0.2 O.D. as recorded at 234 nm. After initial absorbance was recorded, the spectrophotometer was set to zero against blank, and the increase in absorbance during LDL or HDL oxidation was recorded every 10 minutes. The lag time required for the initiation of lipoprotein oxidation was calculated from the oxidation curve.

LDL aggregation

LDL (100 $\mu$g of protein/mL) was mixed by vortex at a fixed strength, and the absorbance at 680 nm was monitored every 10 seconds against a blank solution (41).

LDL retention

Human LDL isolated before and after one or two weeks of pomegranate juice supplementation was used in the ex vivo studies, whereas in the in vitro studies LDL was preincubated with increasing concentrations of pomegranate juice (up to 3.5 $\mu$mol/L of polyphenols) for one hour at 37° C. LDL. 200 $\mu$g of lipoprotein protein/mL were then incubated with chondroitin sulfate (CS, 100 $\mu$g/mL) for 30 minutes at room temperature. The lipoprotein was precipitated with a commercial kit for HDL cholesterol reagent (phosphotungstic acid/$MgCl_2$, Sigma Co, St. Louis, Mo.) that precipitated all the LDL present in the samples followed by a 10-minute centrifugation at 2000×g (42). After discarding the supernatant, the LDL in the precipitate was dissolved in 0.1 N NaOH and analyzed for its glycosaminoglycans (GAGs) content, using the 1,9-dimethylmethylene blue (DMMB) spectrophotometric assay for sulfated glycosaminoglycans (43). Briefly, 2.5 mL of ice-cold DMMB working solution (46 $\mu$mol/L DMMB, 40 mmol/L glycine, 40 mmol/L NaCl in 5% ethanol, adjusted to pH 3.0) was added to 500 $\mu$L of the dissolved precipitate.

The absorbance at 525 nm was then immediately measured. Chondroitin sulfate was used as a standard and was included within each series of assays. A similar preparation of LDL, with no chondroitin sulfate added, was used in parallel as a control. GAGs content obtained in the control was subtracted from the GAGs content in LDL preparations that were incubated with chondroitin sulfate (CS).

Mouse peritoneal macrophages

Mouse peritoneal macrophages (MPM) were harvested from the peritoneal fluid, four days after intraperitoneal injection of 3 mL of thioglycolate (24 g/L, in saline) into each mouse (44). The harvested cells (10–20×$10^6$/mouse)

were washed and centrifuged three times with PBS at 1000 ×g for 10 minutes. Then the cells were resuspended to $10^9$/L in DMEM containing 10% horse serum (heat-inactivated at 56° C. for 30 minutes), 100 U/mL penicillin, 100 µg/mL streptomycin, and 2 mmol/L of glutarmine.

The cell suspension was dispensed into 35 mm plastic Petri dishes and incubated in a humidified incubator (5% $CO_2$, 95% air) for two hours. The dishes were washed once with 5 mL of DMEM to remove nonadherent cells, and the monolayer was further incubated under similar conditions for 18 hours, prior to analyses of various macrophage functions.

Macrophage glutathione content

Cells ($2 \times 10^6$/lmL of PBS) were sonicated twice, for 20 seconds each time, at 80 watts. Cellular protein content was determined using the Folin phenol reagent method (39). For total glutathione analysis, 5% sulfosalicylic acid was added to the supernatant of the sonicated cells (1:2, v:v), followed by cell centrifugation at 20,000×g. Glutathione content in all samples was measured in the supernatant by the 5,5-dithiobis-2-nitrobenzoic acid (DTNB)-GSSG reductase recycling assay (45).

Superoxide anion release

The production of superoxide anion ($O_2^-$) by mouse peritoneal macrophages was measured as the superoxide dismutase inhibitable reduction of acetyl ferricytochrome C (46). Cells ($2 \times 10^6$/well) were suspended in 1 mL of Hanks' Balanced Salts Solution (HBSS) containing acetyl ferricytochrome C (150 µmol/L). Superoxide production by the cells was stimulated by the addition of LDL (100 µg protein/m L) and 5 µumol/L $CUSO_4$, for one hour.

To some control samples, superoxide dismutase (SOD, 30 µg/mL) was added. The amount of superoxide release was determined in the medium and was expressed as nmoles of superoxides/mg cell protein, using an extinction coefficient of $E_{550} = 21$ $mM^{-1}$ $cm^{-1}$.

LDL oxidation by macrophages

Mouse peritoneal macrophages (MPM, $2 \times 10^6$/35mm dish) were incubated with LDL (100 µg of protein/mL) in RPMI medium (phenol-free) in the presence of 2 µmol/L of $CUSO_4$ for six hours. LDL was also incubated under similar conditions in the absence of cells. The extent of LDL oxidation was measured directly in the medium (after centrifugation at 1000×g for 10 minutes in order to spin down detached cells) by the TBARS assay (34). Macrophage-mediated oxidation of LDL was calculated by subtraction of the oxidation rate in the absence of cells from that obtained in the presence of macrophages (47).

Cellular uptake of lipoproteins by macrophages

LDL was radioiodinated by the iodine monochloride method, as modified for lipoproteins (48). Radioiodinated oxidized LDL ($^{125}$I-Ox-LDL) was prepared from $^{125}$I-LDL that was dialysed against PBS, followed by incubation with 5 µmol/L of $CuSO_4$, at 37° C. for 24 hours. $^{125}$I-LDL or $^{125}$-Ox-LDL (10 µg of protein/mL) was incubated with the cells at 37° C. for five hours. Lipoproteins cellular degradation was measured in the collected medium as the trichloroacetic acid (TCA)-soluble, non-lipid radioactivity, which was not due to free iodide (49). Lipoprotein degradation in a cell-free system, measured under identical conditions, was minimal (less than 10%) and was subtracted from the total degradation. The remaining cells were washed three times with cold PBS and dissolved in 0.1 N NaOH for protein and cell-associated lipoproteins determination. Cellular binding of $^{125}$I-Ox-LDL was determined after incubation of the cells with increasing concentrations of $^{125}$I-Ox-LDL or $^{125}$I-LDL at 4° C. for four hours. Then the cells were washed with cold PBS on ice, dissolved in 0.1 N NaOH, and samples were taken to measure radioactivity.

Platelet aggregation

For platelet studies, venous blood (10 mL) was collected through siliconized syringes into 3.8% sodium citrate, at a ratio of 9:1 (v:v). Platelet-rich plasma (PRP) was prepared by low-speed centrifugation (100×g for 10 minutes) at 25° C., and the remaining sample was recentrifuged at 1000×g for 10 minutes to obtain platelet-poor plasma (PPP) (50). Collagen (Nycomed Arzneimittel, Munchen, Germany) was used as the aggregating agent at a concentration of 2 µg/mL, as this concentration caused up to 75% aggregation amplitude. Platelet aggregation was performed at 37° C. in a PAP-4 computerized aggregometer, using platelet poor plasma (PPP) as a reference system for PRP. In the in vitro studies, increasing concentrations of pomegranate juice were incubated for 10 minutes with 1 mL of PRP prior to analyses of platelet aggregation. Results were expressed as the slope of the aggregation curve and are given as cm/min.

Free radical scavenging capacity

DPPH (1,1-diphenyl-2-picryl-hydrazyl) is a radical-generating substance which is widely used to monitor free radical scavenging abilities of various antioxidants (51). To analyze free radical scavenging capacity, increasing concentrations of pomegranate juice (0–14 µmol/L of polyphenols) were mixed with 3 mL of 0.1 mmol DPPH/L in ethanol. The time course for the change in optical density at 517 nm was kinetically monitored (51).

Statistics

Student's paired test was performed for all statistical analyses. Results are given as mean±S.D. for the in vitro studies and as mean±S.E.M. for the in vivo studies. For the in vitro experiments described in FIGS. 1A, 2A and 3, only one experiment, representative of three different experiments performed, is shown. The degree of variation between the three experiments ranged between 7%–9%. The computer software program STATEASE (version 1.00; Data Plus Systems Inc., New York) was used for computation.

RESULTS

The present invention analyzed the antioxidative capacity against lipid peroxidation and the antiatherogenicity of pomegranate juice, which is rich in some specific polyphenols, in vitro and ex vivo, in healthy human volunteers and in the atherosclerotic apolipoprotein E deficient mice, which are under oxidative stress. The results are set forth below.

I. In vitro studies

To study the effect of pomegranate juice in vitro on the susceptibility of plasma to lipid peroxidation, plasma from healthy volunteers was incubated with 100 mmol/L of the free radical generator AAPH for two hours at 37° C. in the presence of increasing concentrations of pomegranate juice.

FIG. 1 shows the effect of pomegranate juice on AAPH-induced plasma lipid peroxidation. Normal human plasma (diluted ×2 in PBS) was incubated with increasing pomegranate juice concentrations (0–1.5 µmol of polyphenols/L), in the absence or presence of 100 mmol/L of AAPH for two hours at 37° C. The extent of plasma lipid peroxidation was measured by the TBARS assay (A) and by the lipid peroxides assay (B). Values obtained in the absence of AAPH were subtracted from those obtained in the presence of AAPH. Results are given as mean±S.D. (n=3).

FIG. 1 demonstrates that pomegranate juice inhibits AAPH-induced plasma lipid peroxidation in a dose-dependent manner. A 46% inhibition in thiobarbituric acid reactive substances (TBARS) formation (FIG. 1A) and a 21% inhibition in lipid peroxides formation (FIG. 1B) was obtained upon using a concentration of 0.17 mL/L of pomegranate juice, which is equivalent to 0.5 µmol of total polyphenols/L.

Figure 2:
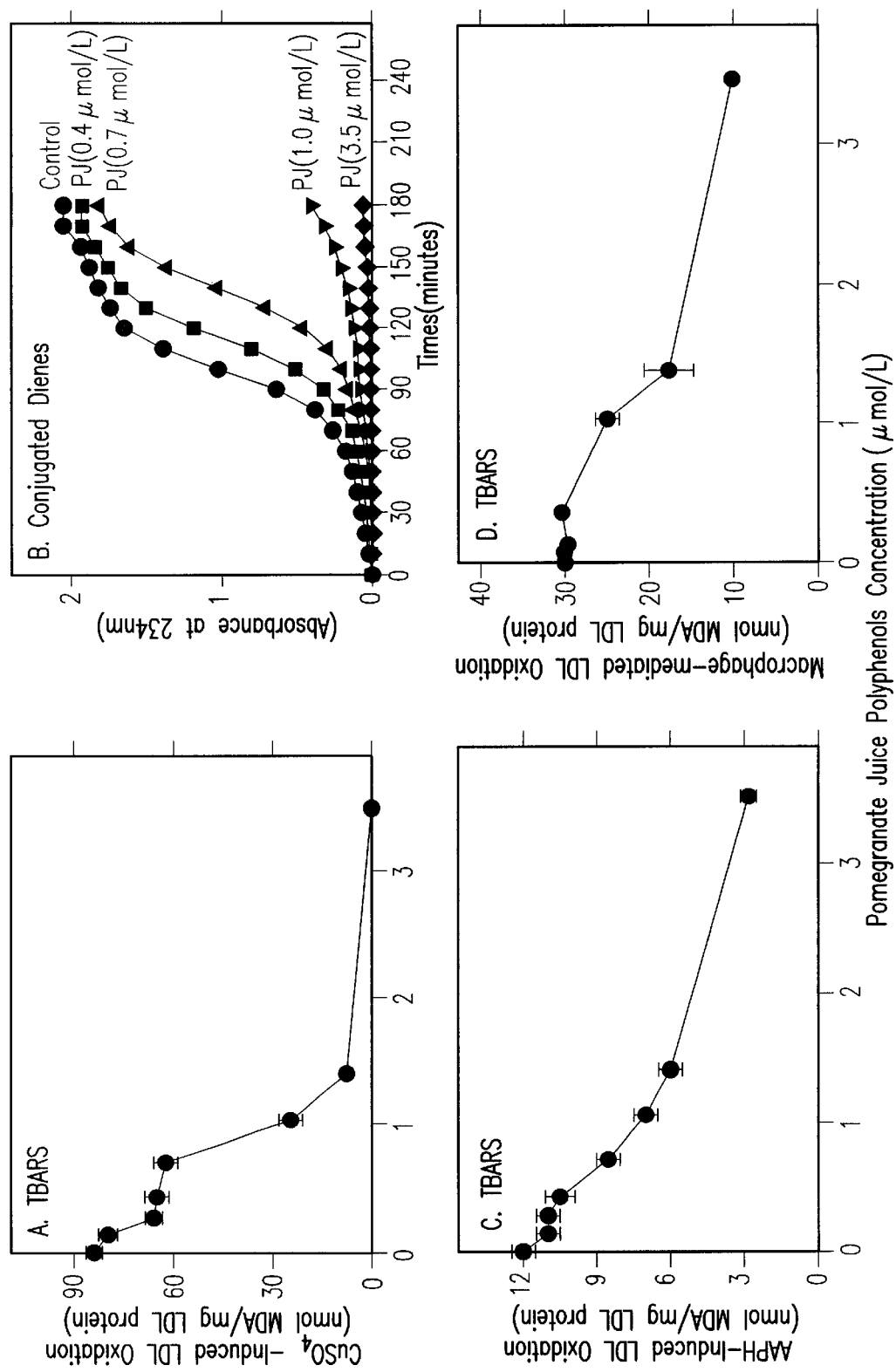
FIG. 2 shows the effect of pomegranate juice on LDL susceptibility to oxidation: concentration study.

FIG. 2 shows the effect of pomegranate juice on LDL susceptibility to oxidation: concentration study. LDL (100 µg of protein/mL) was incubated with increasing concentrations of pomegranate juice (0–3.5 µmol/L of polyphenols). LDL oxidation was induced by its incubation with 5 µmol/L $CuSO_4$, and was measured as TBARS formation after two hours of incubation (A), or as conjugated dienes formation, kinetically monitored at 234 nm (B). LDL oxidation was also induced by 5 mmol/L of AAPH (C) or by J-774 A.1 macrophages in the presence of 2 µmol/L $CuSO_4$ (D) and measured as TBARS formation. Results are given as mean±S.D. (n=3). PJ, pomegranate juice.

The susceptibility of isolated LDL to oxidation induced by copper ions was substantially inhibited by pomegranate juice in a dose-dependent manner, as demonstrated by a reduction in TBARS formation (FIG. 2A) and a prolongation of the lag time required for the initiation of LDL oxidation by 40 minutes (FIG. 2B), upon using of 0.24 mL pomegranate juice/L (equivalent to 0.7 µmol polyphenols/L). On using 3.5 mL of pomegranate juice/L (equivalent to 1 µmol of polyphenols/L), the initiation of LDL oxidation was not achieved even after 180 minutes. Similarly, pomegranate juice dose-dependently inhibited LDL oxidation induced either by the radical generator AAPH (FIG. 2C) or by J-774 A.1 macrophages (FIG. 2D).

Figure 3:
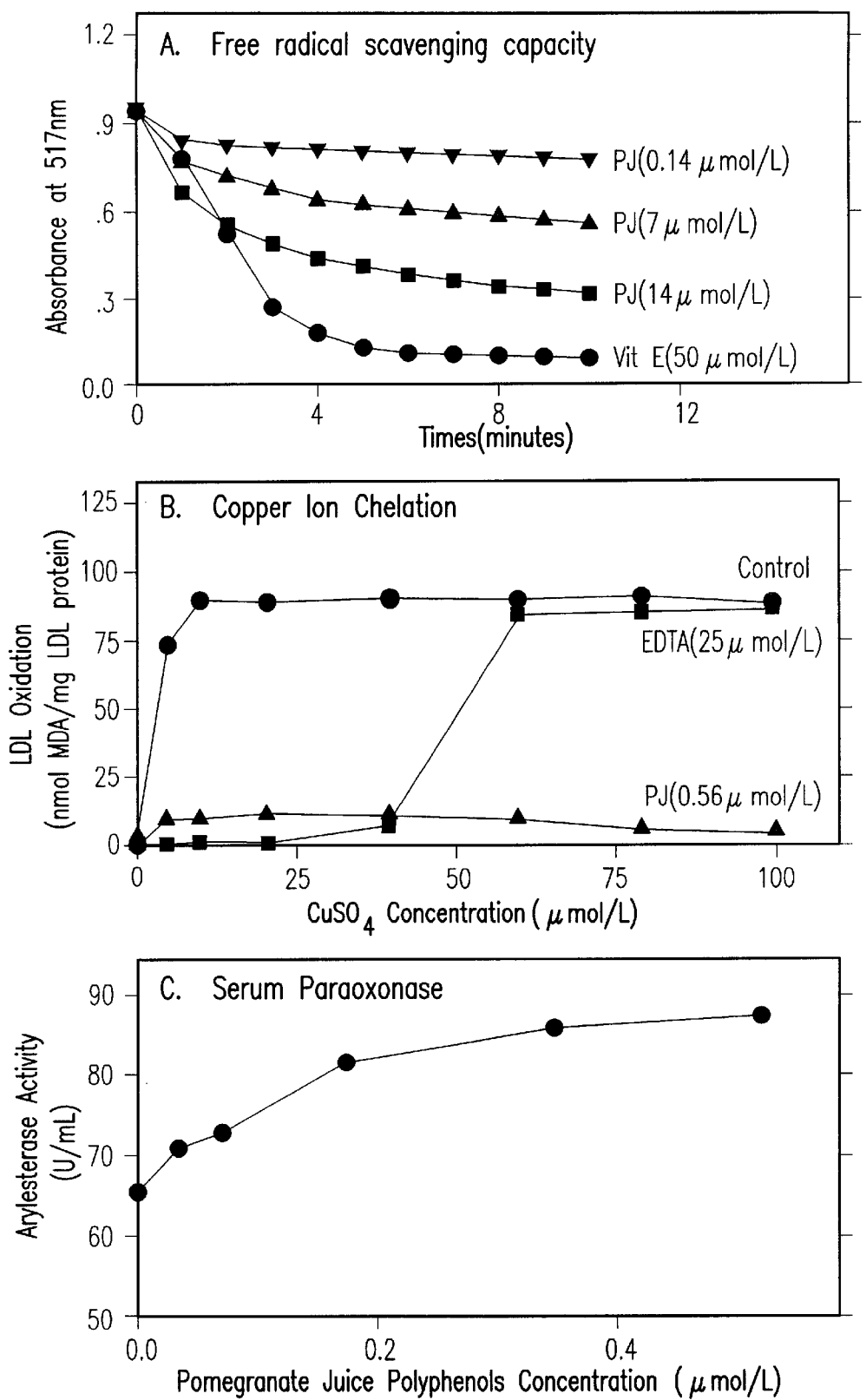
FIG. 3 shows the mechanisms for pomegranate juice protection against LDL oxidation.

To study the mechanism responsible for the antioxidative capacity of pomegranate juice in vitro, the present invention analyzed the potency of pomegranate juice to scavenge free radicals, to chelate transition metal ions, or to increase serum paraoxonase activity. FIG. 3 shows the mechanisms for pomegranate juice protection against LDL oxidation. FIG. 3(A) shows the free radical scavenging capacity of pomegranate juice. 1,1-diphenyl-2-picrylhdrazyl (DPPH) ethanolic solution at a final concentration of 100 µmol/L was mixed with increasing concentrations (0–14 µmol of polyphenols/L) of pomegranate juice (PJ), or with 50 µmol/L of vitamin E. The time course of the changes in absorbance was continuously monitored at 517 nm. FIG. 3(B) shows the copper-ions chelating capacity of pomegranate juice. LDL (100 µg of protein/mL) was incubated with increasing concentrations of $CuSO_4$ (0–100 µmol/L) in the absence (Control) or presence of $Na_2$ EDTA (EDTA) and 0.25 µmol/L or 0.56 µmol of pomegranate juice (PJ), polyphenols/L for two hours at 37° C. The extent of LDL oxidation was measured by the TBARS assay. FIG. 3(C) shows the effect of pomegranate juice on serum paraoxonase activity. Increasing concentrations of pomegranate juice (0–0.5 µmol of polyphenols/L) were added to human serum (obtained from normolipidemic volunteers) and incubated for 10 minutes at 37° C. before measuring arylesterase activity. Results represent mean±S.D. (n=3).

FIG. 3A shows that the addition of 4.9 mL of pomegranate juice/L (14 µmol of polyphenols/L) to a DPPH solution induced a dose-dependent decrease in the absorbance at 517 nm, which reached a plateau within 7 minutes of incubation. This is a pattern similar to that obtained with 50 µmol/L of vitamin E, which is a potent free radical scavenger (FIG. 3A). In order to examine whether pomegranate juice inhibits LDL oxidation by chelation of metal ions, LDL (100 mg of protein/(L) was incubated with 0.2 mL of pomegranate juice/L (0.56 µmol of polyphenols/L) in the presence of increasing concentrations of copper ions. Incubation of LDL with 25 µmol/L of $Na_2$ EDTA served as a positive control, as EDTA is a potent chelator of metal ions. FIG. 3B demonstrates the 25 µmol/L of EDTA inhibited copper ion-induced LDL oxidation upon using up to 40 µmol/L of $CuSO_4$. At higher copper ion concentrations, EDTA could no longer overcome the pro-oxidative effect of $CuSO_4$. In contrast, 0.2 mL/L of pomegranate juice (0.56 µmol/L of polyphenols) inhibited $CuSO_4$-induced LDL oxidation even at a $CuSO_4$ concentration as high as 80 µmol/L (FIG. 3B), suggesting that pomegranate juice does not chelate copper ions.

HDL-associated paraoxonase (PON 1) activity in serum is related to protection of LDL against oxidation. Upon incubation of human serum with increasing concentrations of pomegranate juice for 10 minutes at 37° C., pomegranate juice dose-dependently increased serum PON 1 activity by up to 33% (FIG. 3C). These results suggest that pomegranate juice inhibits plasma LDL lipid peroxidation in vitro, and this effect is associated with its capacity to scavenge free radicals, as well as to increase serum PON 1 activity.

Analyses of antioxidant properties against LDL oxidation of pomegranate constituents other than the juice include the pomegranate outer and inner peels and its seeds. We thus prepared aqueous solutions of the peels and the crushed seeds. Polyphenols analysis of the aqueous solutions of the concentrated pomegranate juice, the inner and outer peels and the seeds revealed that they contain: 22,830, 10,320, 6314 and 630 µM of total polyphenols, respectively.

Figure 4:
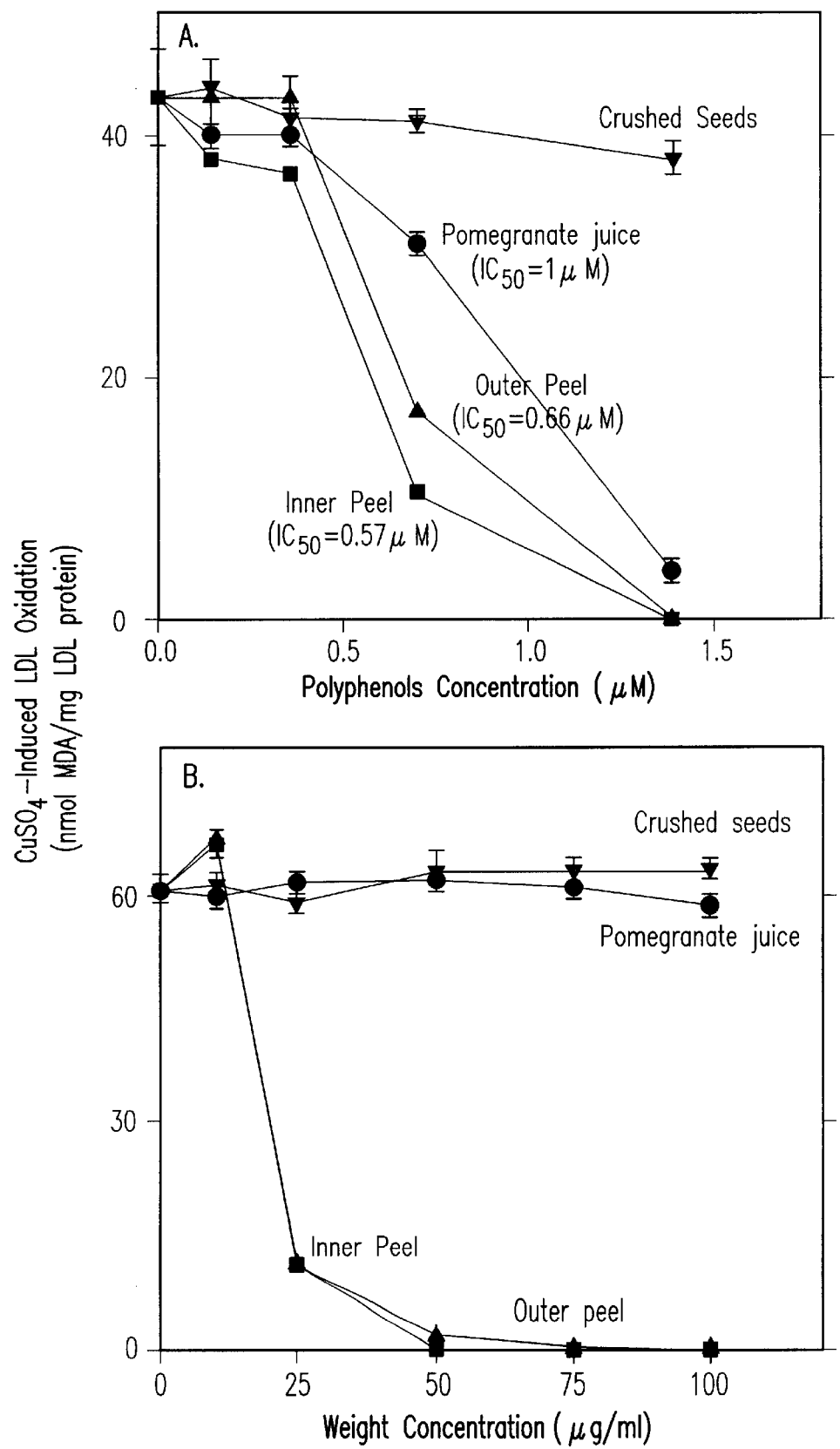
FIG. 4 shows the capacity of pomegranate constituents (juice, peels and seeds) to inhibit copper ion-induced LDL oxidation.

On comparing the inhibitory effects of these pomegranate constituents, based on equal polyphenols concentration, it was demonstrated that the aqueous extracts of the inner and outer peels were more powerful antioxidants, in comparison to the juice. This data suggests that they may contain more potent antioxidant polyphenols. FIG. 4 shows the capacity of pomegranate constitutents juice, peels and seeds) to inhibit copper ion-induced LDL oxidation. In FIG. 4(A), aqueous extracts of pomegranate juice (crushed seeds, inner and outer peels) were prepared. The amount of total polyphenols was determined as described under "Methods". LDL (100 µg of protein/ml) was incubated with increasing polyphenols concentration (0–1.5 µM) of pomegranate juice, or aqueous extracts of crushed seeds, inner and outer peels, for two hours at 37° C. in the presence of 5 µM $CuSO_4$. In FIG. 4(B), the pomegranate juice and the aqueous extracts of crushed seeds, inner and outer peels were lyophylized and their dry weight measured. All samples were dissolved in water and diluted to 1 mg of weight/ml. LDL (100 µg of protein/ml) was then incubated with increasing concentrations (0–100 µg weight/ml) of the pomegranate fractions for two hours at 37° C. in the presence of 5 µM $CuSO_4$. LDL oxidation was analyzed by the TBARS assay. Results represent mean±S.D. (n=3).

FIG. 4(A) shows that the concentrations of polyphenols, which were required to inhibit LDL oxidation by 50% ($IC_{50}$), were 0.56 and 0.66 µM for the inner peel and outer peel, respectively, compared to 1.00 µM that was obtained for the juice (FIG. 4A). The aqueous extract obtained from the crushed seeds was found to be a weak antioxidant against LDL oxidation (FIG. 4A).

It is possible that other substances except polyphenols can contribute to the antioxidant activity of the pomegranate constituents; thus the present invention analyzed the effect of increasing weight concentrations (0–100 µg/ml, FIG. 4B), rather than that of the total polyphenols content (FIG. 4A) on copper ions-induced LDL oxidation. The inner and outer peels contain potent antioxidants in comparison to the crushed seeds and the pomegranate juice, which showed no inhibitory effects at the concentrations used (FIG. 4B). Per 1 mg of weight, the inner and outer peels contain 20–30-fold more polyphenols than the aqueous fractions of the seeds and the pomegranate juice (566 and 739 nmole of polyphenols per mg weight vs. 22 and 25 nmol of polyphenols per mg weight, respectively).

The ineffectiveness of the pomegranate juice to inhibit LDL oxidation in this study (FIG. 4B), in comparison to its potency shown in the previous study (FIG. 4A), can possibly be related to the much lower total polyphenols concentrations (about 900-fold) of PJ that was used for the study presented in FIG. 4, compared to that used for the study shown in FIG. 4A.

II. Ex vivo studies

Antioxidative effects of pomegranate juice were tested ex-vivo in two systems: healthy humans and atherosclerotic mice. For the human study, 13 healthy, non-smoking men were supplemented with 50 mL/day of pomegranate juice (contains 1.5 mmoles of total polyphenols) for a period of two weeks. The studies on the atherosclerotic apolipoprotein E deficient (E°) mice included dietary supplementation with 6.25 or 12.5 $\mu$L of pomegranate juice/mouse/day (equivalent to 0.175 or 0.350 $\mu$moles of total polyphenols, respectively), and were analyzed in comparison to a control placebo-treated group (water consumption with no pomegranate juice added).

A. Plasma lipid pattern

Pomegranate juice administration to healthy men for a period of two weeks had no significant effect on plasma lipid profiles, including total cholesterol concentration, LDL-cholesterol, VLDL-cholesterol, HDL-cholesterol and triglycerides (Table 1). Post-prandial samples obtained from three of the volunteers after two or four hours of pomegranate juice consumption revealed no significant effect on all major routine chemistry, hematology and coagulation assays (data not shown). Similarly, no significant effect could be demonstrated on plasma lipids concentrations in the E° mice that consumed pomegranate juice, in comparison to control mice that consumed only water (data not shown).

TABLE 1

Effect of pomegranate juice supplementation on plasma lipids and lipoproteins pattern.

| | Time after Pomegranate juice supplementation | | |
|---|---|---|---|
| | 0 (Before) | 1 week | 2 weeks |
| Total cholesterol | 194 ± 14 | 200 ± 14 | 204 ± 12 |
| LDL - cholesterol | 121 ± 10 | 122 ± 9 | 136 ± 11 |
| VLDL - cholesterol | 27 ± 4 | 30 ± 5 | 28 ± 2 |
| HDL - cholesterol | 43 ± 3 | 42 ± 3 | 39 ± 2 |
| Triglycerides | 136 ± 21 | 149 ± 22 | 144 ± 12 |

Results are given as mg/dl and expressed as mean±S.D. (n=13).

B. Plasma lipid peroxidation

Human plasma, obtained after two weeks of pomegranate juice consumption, demonstrated a small but significant ($p<0.01$) 6% decreased susceptibility to AAPH-induced lipid peroxidation, in comparison to plasma obtained prior to pomegranate juice consumption, as measured by lipid peroxides formation.

Figure 5:
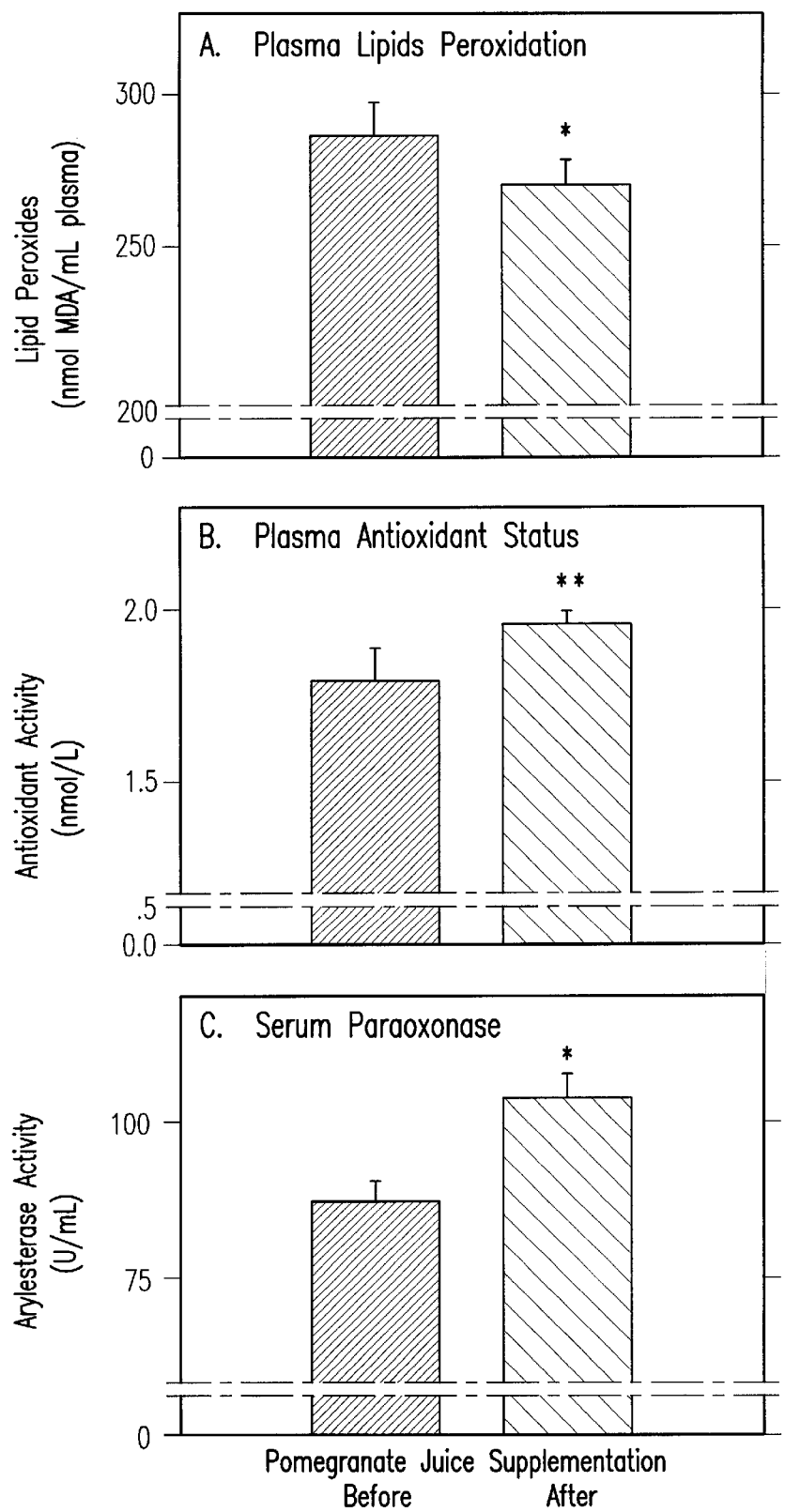
FIG. 5 shows the effect of pomegranate juice supplementation on human plasma oxidative state in ex vivo studies.

FIG. 5 shows the effect of pomegranate juice supplementation on human plasma oxidative state in ex vivo studies. Blood was obtained from 13 subjects before or after two weeks of pomegranate juice supplementation. FIG. 5(A) shows the susceptibility of plasma to AAPH-induced lipid peroxidation. Plasma samples were diluted (×2) in PBS and lipid peroxidation was induced by incubation with 100 mmol/L of AAPH for two hours at 37° C. The extent of plasma lipid peroxidation was determined by the lipid peroxides assay. In FIG. 5(B), plasma total antioxidant status was measured by a commercially available kit, as described under "Methods". In FIG. 5(C), serum paraoxonase was determined by measuring arylesterase activity. Results represent mean±S.D. (n=3)*$p<0.01$, ** $p<0.05$ (After vs. Before).

FIG. 5A shows a significant ($p<0.05$) 9% increment in plasma total antioxidant status two 2 weeks of pomegranate juice consumption, in comparison to plasma derived before juice consumption (FIG. 5B).

Plasma oxidative state studied in three of the volunteers was not affected after two and four hours of pomegranate juice consumption as determined by total antioxidant status (TAS) and AAPH-induced lipid peroxidation (data not shown). A significant ($p<0.01$) 18% increase in serum paraoxonase (PON 1) activity was monitored after pomegranate juice consumption for a period of two weeks (FIG. 5C). As serum paraoxonase is bound to HDL, it was questioned whether the increased serum paraoxonase activity following pomegranate juice consumption is associated with increased resistance of HDL to oxidation.

Figure 6:
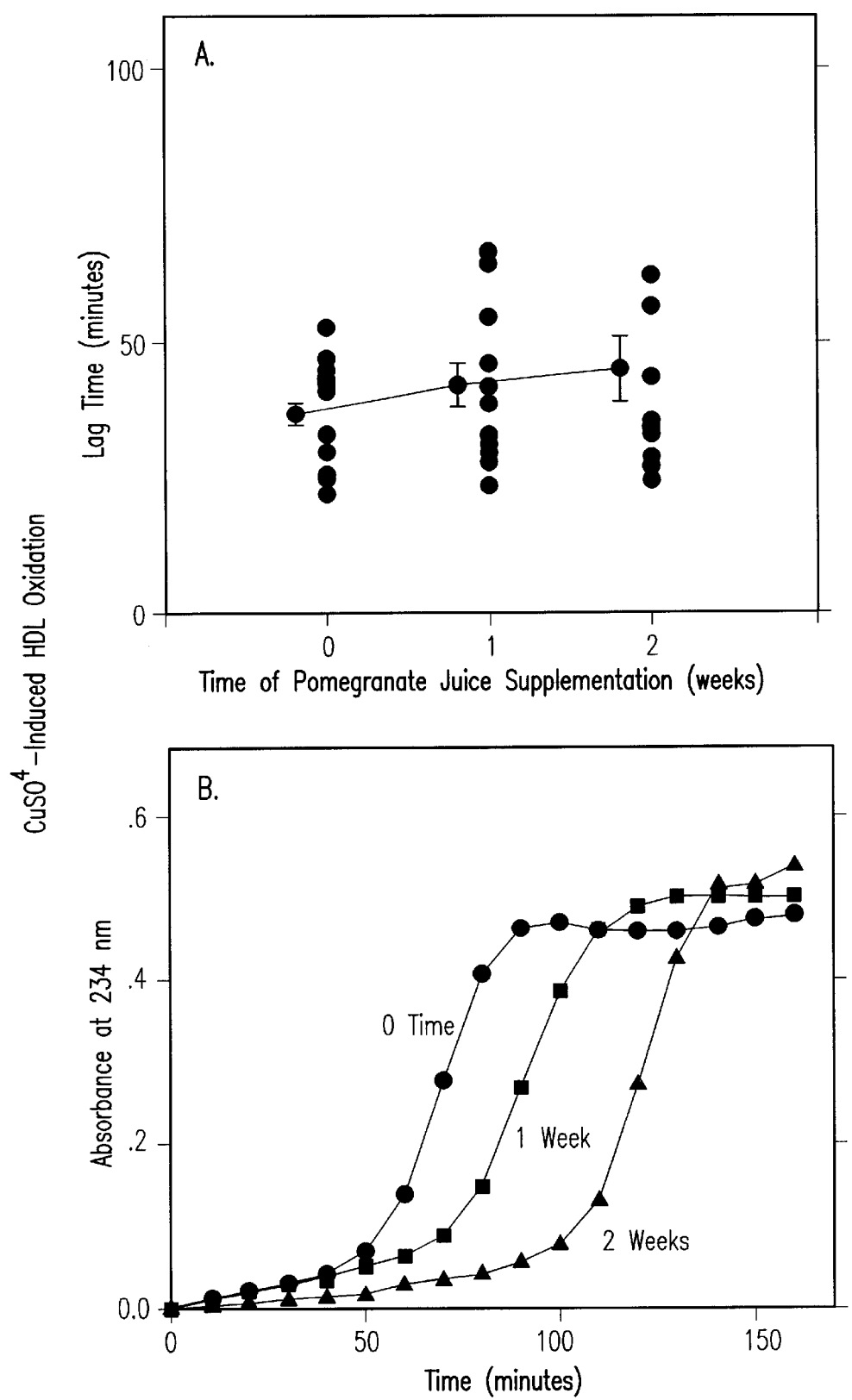
FIG. 6 shows the effect of pomegranate juice supplementation to humans on the susceptibility of their HDL to oxidation in ex-vivo studies.

FIG. 6 shows the effect of pomegranate juice supplementation to humans on the susceptibility of their HDL to oxidation in ex-vivo studies. FIG. 6(A) shows the susceptibility to oxidation of HDL obtained from 12 healthy volunteers before (0) or after one week or two weeks of pomegranate juice supplementation. HDL (100 $\mu$g of protein/mL) was incubated with 5 $\mu$mol/L $CuSO_4$ for three hours at room temperature. The formation of conjugated dienes was kinetically monitored at 234 nm and the lag time was measured. Results represent the mean±S.D. (n=12). FIG. 6 (B) is a representative figure of HDL oxidation before and after one week or two weeks of pomegranate juice supplementation.

Pomegranate juice consumption (50 mL/day) for a period of two weeks gradually increased the resistance of HDL to copper ion-induced oxidation as shown by a prolongation in the lag time required for the initiation of HDL oxidation (FIG. 6A) from 37±2 minutes to 45±6 minutes before and two weeks after PJ consumption, respectively. FIG. 6B shows a representative kinetic analysis of copper ion-induced oxidation of HDL derived before study entry, and after one and two weeks consumption of pomegranate juice.

Figure 7:
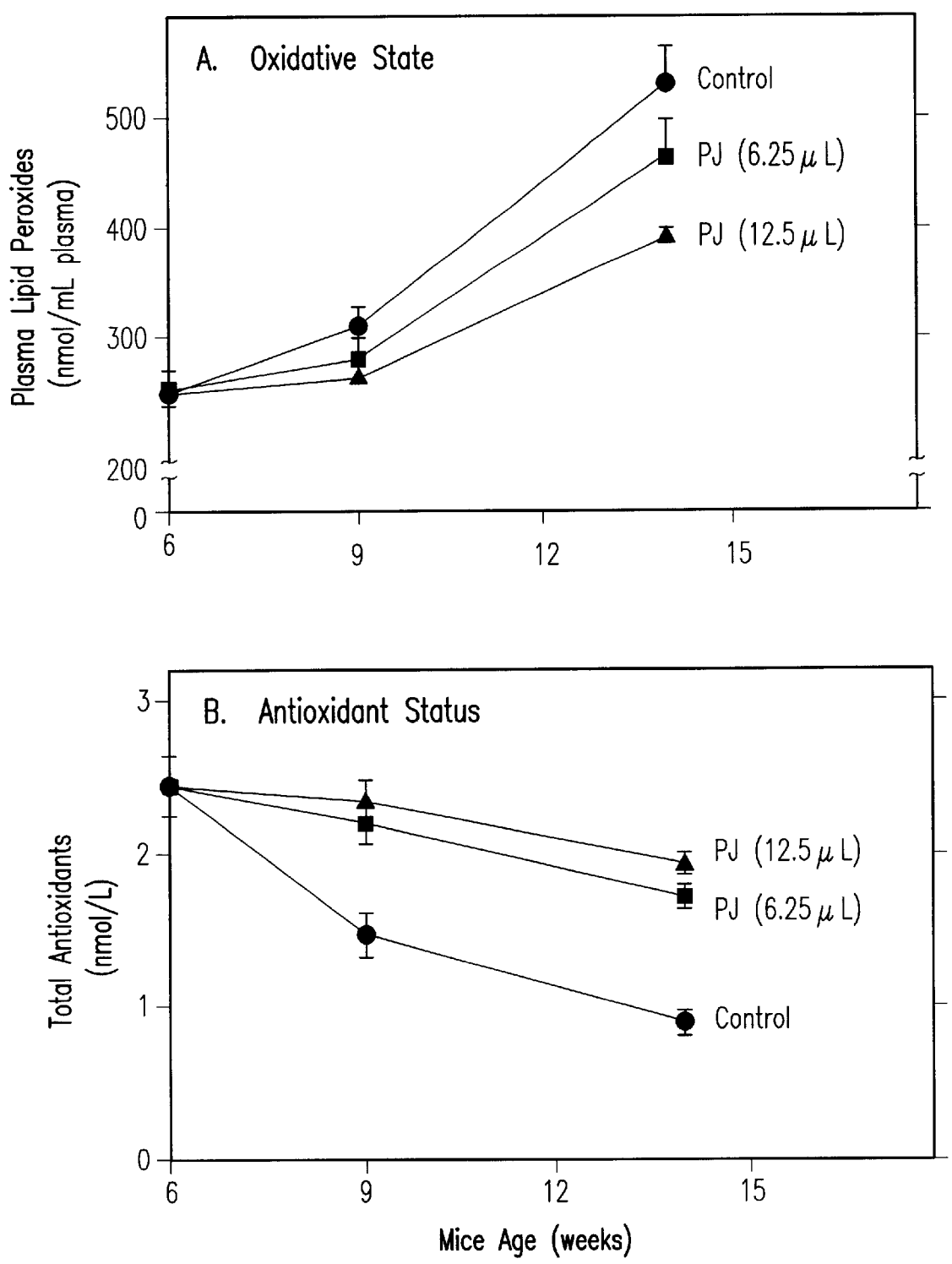
FIG. 7 shows the effect of pomegranate juice supplementation to E° mice on their plasma oxidative stress during aging.

Pomegranate juice consumption exhibited antioxidative effects also when administered to E° mice. FIG. 7 shows the effect of pomegranate juice supplementation to E° mice on their plasma oxidative stress during aging. E° mice (10 mice in each group) at the age of 6 weeks were supplemented with placebo (Control) or with 6.25 or 12.5 $\mu$L (equivalent to 0.175 or 0.350 $\mu$mols of total polyphenols, respectively) of pomegranate juice (PJ). Blood samples were drawn at the age of 6, 9 and 14 weeks. In FIG. 7(A), the plasma oxidative state was determined by measuring the levels of lipid peroxides in plasma samples. In FIG. 7(B), the antioxidant status of the plasma samples was measured using a commercial kit. Results represent the mean±S.D. (n=3). PJ, pomegranate juice.

The basal oxidative state, measured as lipid peroxides in plasma of control E° mice (that did not consume pomegranate juice), increased gradually during aging from 260 nmol/mL of plasma at 6 weeks of age, to 309 and 535 nmol/mL of plasma at 9 and 14 weeks of age, respectively (FIG. 7A). Following pomegranate juice consumption, plasma lipid peroxidation was markedly reduced, and this effect was pomegranate juice concentration-dependent (FIG. 7A). Similarly, serum total antioxidant status was higher in E° mice that consumed pomegranate juice in comparison to control mice, and this effect was again juice concentration-dependent (FIG. 7B). Serum paraoxonase activity decrement during aging in the atherosclerotic E° mice, which are under excess oxidative stress (13), however. was not protected by pomegranate juice consumption (data not shown).

C. LDL modifications (oxidation, aggregation, retention)
a. LDL oxidation

Figure 8:
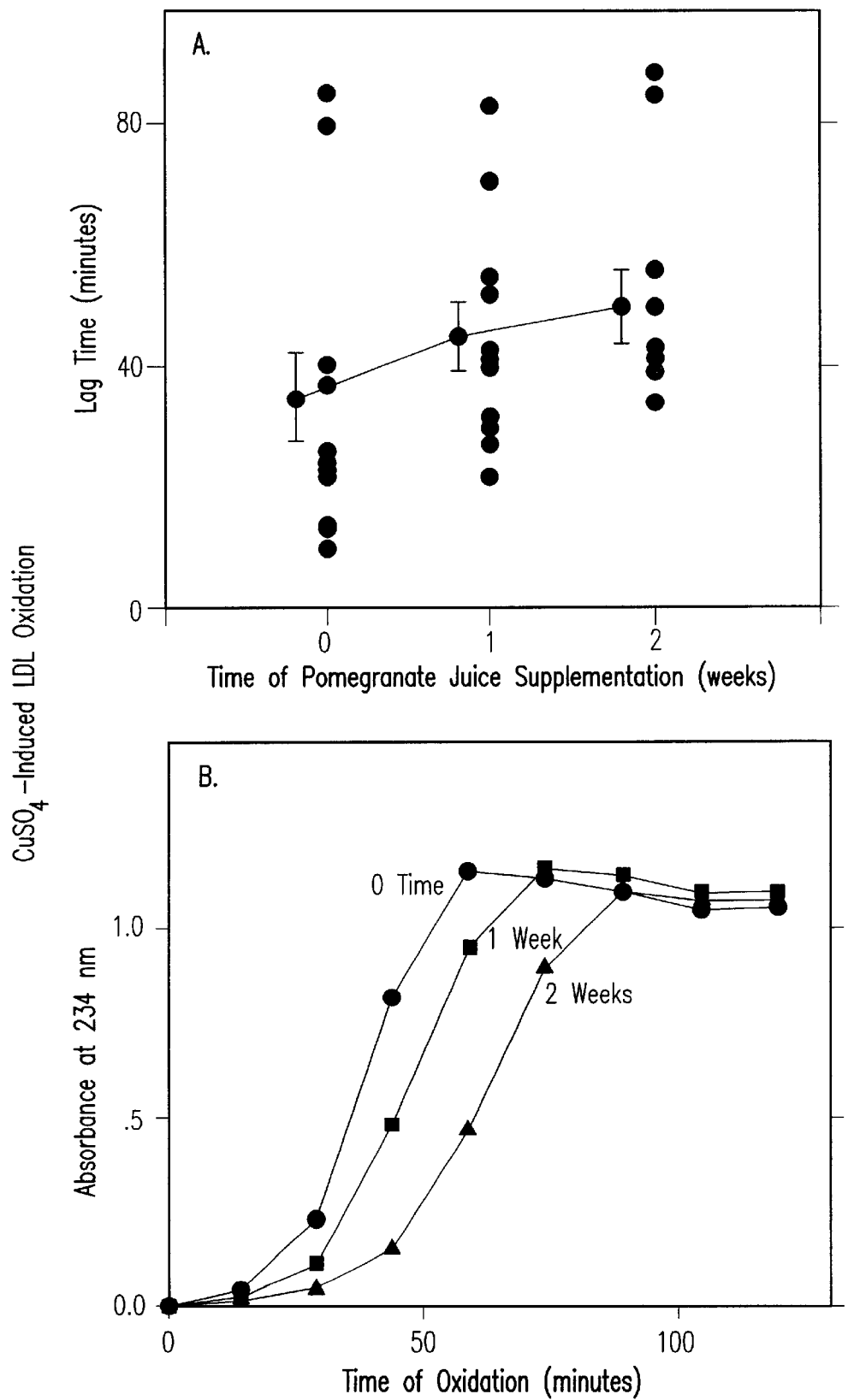
FIG. 8 shows the effect of pomegranate juice supplementation to humans on the susceptibility of their LDL to oxidation in ex-vivo studies.

FIG. 8 shows the effect of pomegranate juice supplementation to humans on the susceptibility of their LDL to oxidation in ex-vivo studies. In FIG. 8(A), LDL (100 $\mu$g of protein/ml) obtained from 12 healthy volunteers before (0) or after one week or two weeks of pomegranate juice supplementation was incubated with 5 $\mu$mol/L $CuSO_4$ for three hours at room temperature. The formation of conjugated dienes was kinetically monitored at 234 nm and the lag time was measured. Results are given for each individual, as well as the mean±S.D. (n=12). In FIG. (B), a representative experiment of LDL oxidation, before and after one week or two 15 weeks of pomegranate juice supplementation, is shown.

The susceptibility of LDL (derived from healthy volunteers after consumption of pomegranate juice for one and two weeks) to copper ions-induced oxidation was found to be gradually reduced, as shown by a prolongation of the lag time required for the initiation of LDL oxidation by 29% and 43%, in comparison to LDL obtained prior to juice consumption (from 35±6 minutes before juice consumption to 44±6 minutes and 50±6 minutes after consumption of pomegranate juice for one and two weeks, respectively, FIG. 8A). A representative kinetic analysis of copper ion-induced LDL oxidation from this study is shown in FIG. 8B.

Figure 9:
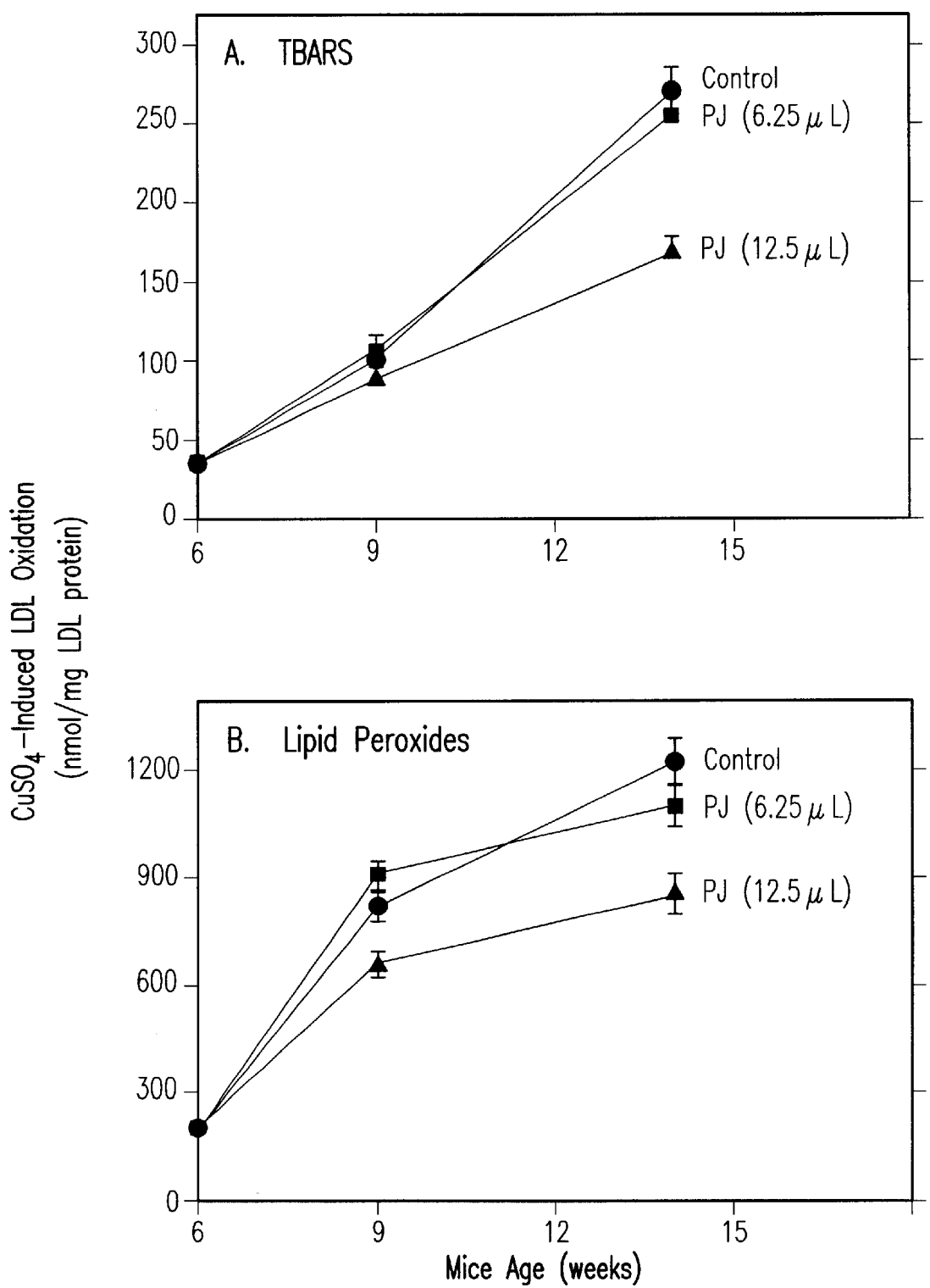
FIG. 9 shows the effect of pomegranate juice supplementation to E° mice on their LDL susceptibility to copper ions-induced oxidation in ex-vivo studies.

Pomegranate juice consumption also reduced the propensity of E° mice-derived LDL to copper ion-induced oxidation. In E° mice that consumed 6.25 $\mu$L/day or 12.5 $\mu$L/day of pomegranate juice for a period of two months, LDL oxidation was delayed by 100 minutes and by 120 minutes, respectively, in comparison to LDL obtained before juice administration (data not shown). FIG. 9 shows the effect of pomegranate juice supplementation to E° mice on their LDL susceptibility to copper ions-induced oxidation in ex vivo studies. LDLs were isolated from plasma samples that were collected from E° mice (10 mice in each group) that received placebo (Control), or 6.25 $\mu$L or 12.5 $\mu$L of pomegranate juice (PJ) (equivalent to 0.175 or 0.350 $\mu$moles of total polyphenols, respectively), at the age of 6, 9 or 14 weeks. The LDLs (100 $\mu$g of protein/mL) were incubated with 5 $\mu$mol/L $CuSO_4$, for two hours at 37° C. The extent of LDL oxidation was measured by the TBARS (A) or lipid peroxides (B) assays. Results represent mean±S.D. (n=3).

The progressive increase with age in the susceptibility of the mice LDL to oxidation was significantly attenuated by pomegranate juice consumption, in a dose-dependent manner, as shown for both TBARS (FIG. 9A) and lipid peroxides (FIG. 9B) formation.

b. LDL aggregation

Atherogenicity of LDL is attributed not only to its oxidative modification, but also to its aggregation (4). It was previously shown that LDL oxidation leads to its subsequent aggregation (21), and it has been recently reported that polyphenols from red wine can reduce LDL aggregation in vitro and in vivo (23).

Figure 10:
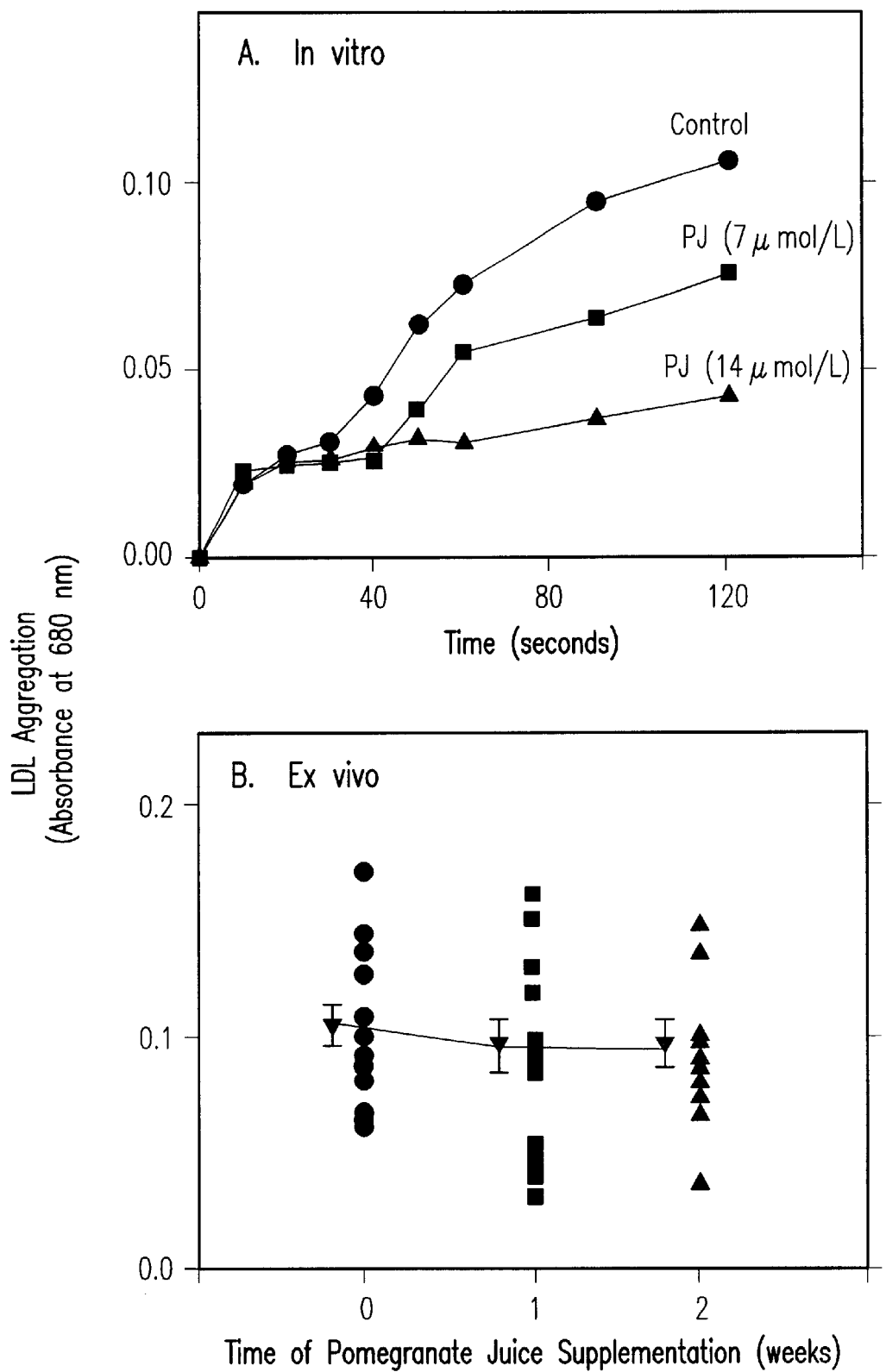
FIG. 10 shows the effect of pomegranate juice on the susceptibility of LDL to aggregation in in vitro and ex-vivo studies.

FIG. 10 shows the effect of pomegranate juice on the susceptibility of LDL to aggregation in in vitro and ex-vivo studies. In FIG. 10(A), LDL (100 $\mu$g of protein/mL) was incubated without (Control) or with 7 $\mu$mol/L or 14 $\mu$mol/L of polyphenols of pomegranate juice (PJ) for 10 minutes at room temperature, before measuring LDL aggregation. LDL aggregation (by vortexing) was kinetically monitored at 680 nm. A representative experiment out of three similar studies is given. In FIG. 10(B), the extent of LDL aggregation was measured in 13 healthy volunteers before (0) and after one week or two weeks of pomegranate juice supplementation. Results are given for each individual as well as the mean±S.D. (n=13).

The addition of increasing concentrations of pomegranate juice to LDL reduced its susceptibility to aggregation (by vortexing) in a dose-dependent fashion (FIG. 10A). Upon analyzing the susceptibility to aggregation of LDL isolated from individual subjects that consumed pomegranate juice for one and two weeks, in 7 out of the 13 subjects studied, a pattern of reduction in LDL aggregation was observed, although the mean value showed no significant changes (FIG. 10B).

C. LDL retention

Figure 11:
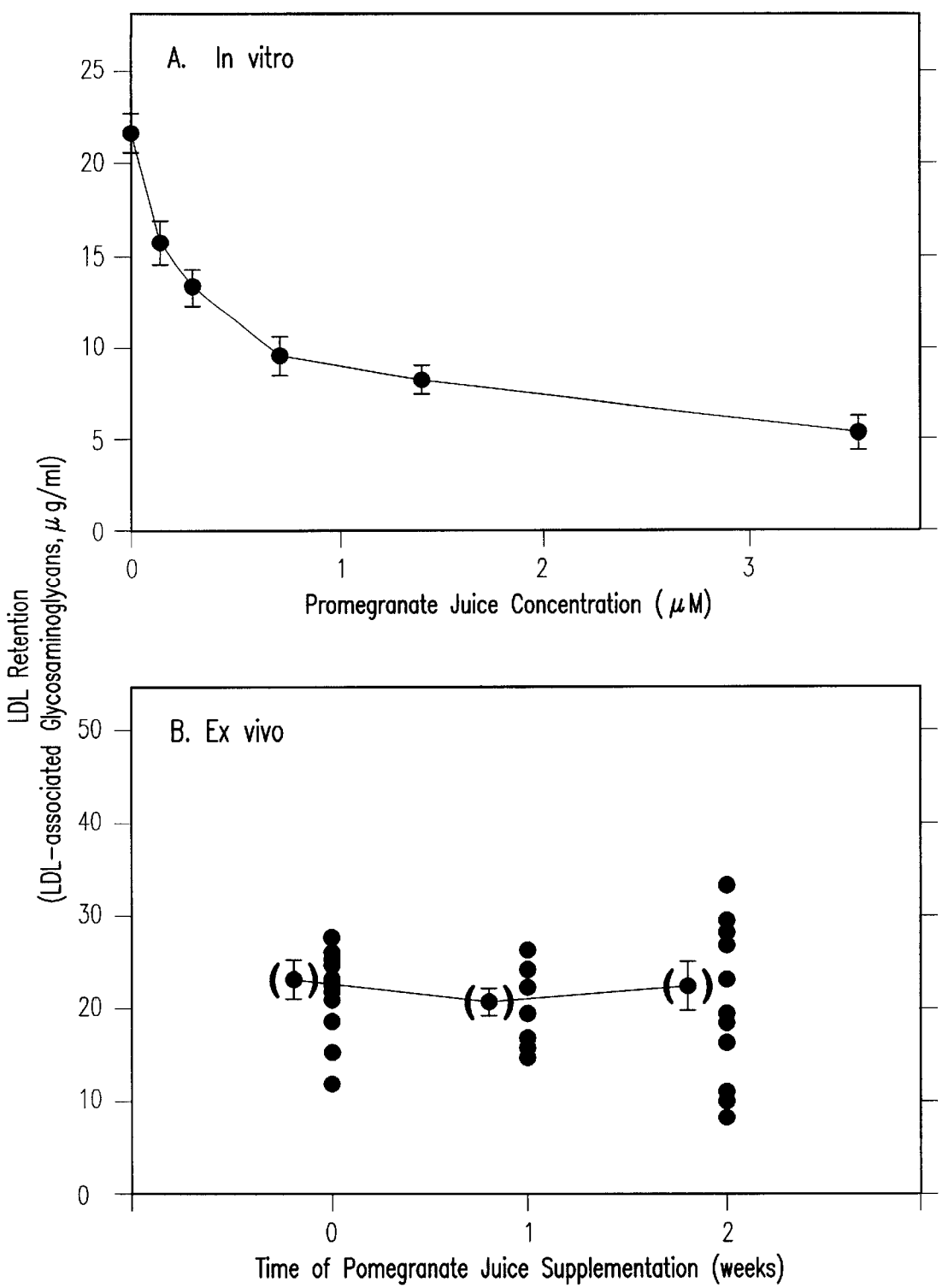
FIG. 11 shows the effect of pomegranate juice on "LDL retention," analyzed by LDL capacity to bind chondroitin sulfate.

Extracellular matrix (ECM) proteoglycans (PGs) can bind LDL through their glycosaminoglycans (GAGs) moieties, and such interaction can lead to the entrapment of LDL in the arterial wall, a phenomenon called "LDL retention" (5). FIG. 11 shows the effect of pomegranate juice on "LDL retention" analyzed by LDL capacity to bind chondroitin sulfate. In FIG. 11(A), LDL (200 $\mu$g of lipoprotein protein/mL) was incubated with increasing concentrations of pomegranate juice (0–3.5 $\mu$mol of polyphenols/L) for one hour at 37° C., followed by the addition of chondroitin sulfate (CS, 100 pg/mL) and a further incubation for 30 minutes at room temperature. LDL was then precipitated, and the LDL-associated GAGs content was analyzed in the precipitate using the DMMB assay as described under "Methods". Results are presented as mean±S.D. In FIG. 11(B), chondroitin sulfate (CS, 100 $\mu$g/mL) was incubated for 30 minutes at room temperature with LDL (200 $\mu$g of lipoprotein protein/mL) isolated from plasma of the studied individuals, before and after one or two weeks of pomegranate juice consumption. Results of "LDL retention" for each individual, as well as the mean±S.D., are presented.

According to FIG. 11, addition of increasing concentrations of pomegranate juice (0–3.5 $\mu$moL of polyphenols/L) to LDL (200 $\mu$g of lipoprotein protein/mL) induced a substantial dose-dependent reduction in the capacity of LDL to bind chondroitin sulfate (CS, 100 $\mu$g/mL). LDL binding to chondroitin sulfate decreased by up to 75%, following its incubation with 3.5 $\mu$mol/L of pomegranate juice polyphenols (FIG. 11A). The capacity of LDLs, obtained from subjects that were supplemented with pomegranate juice, to bind chondroitin sulfate (CS) was also determined, as an indication for their "LDL retention."

The mean value for LDL-associated GAGS was not significantly affected after pomegranate juice consumption (FIG. 11B). Pomegranate juice supplementation for one week and for two weeks affected "LDL retention" only in some of the volunteers with no significant effect on the mean value for all study participants. In 69% and 54% of the cases, a decrease in LDL capacity to bind CS was observed after one week and two weeks of pomegranate juice supplementation, respectively, compared to the results obtained before juice administration (FIG. 11B).

III. Macrophage atherogenicity

It has been recently shown that macrophages can undergo lipid peroxidation under oxidative stress and, subsequently, these cells can oxidize LDL (52, 53). LDL oxidation by macrophages is considered to be a major event during early atherogenesis, and it is associated with cellular uptake of the modified lipoprotein, leading to macrophage cholesterol accumulation and foam cell formation (1). The present invention has thus studied the effect of dietary consumption of pomegranate juice in E° mice on macrophage lipid peroxidation and, subsequently, on macrophage activities related to foam cell formation, including cell-mediated to oxidation of LDL and cellular uptake of lipoproteins.

A. Macrophage-mediated oxidation of LDL

Figure 12:
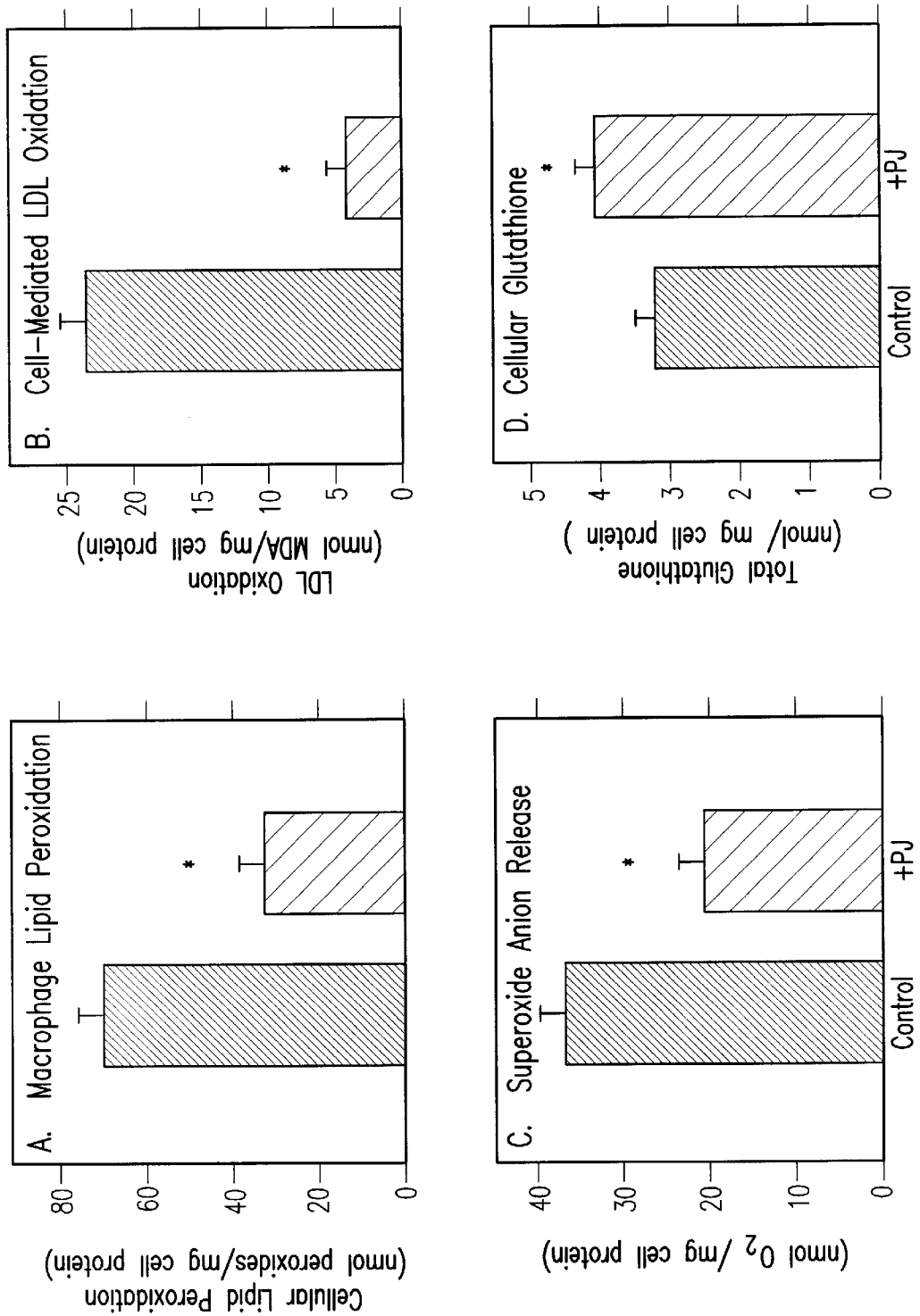
FIG. 12 shows the effect of pomegranate juice consumption by E° mice on their peritoneal macrophage lipids peroxidation and their ability to oxidize LDL.

Mouse peritoneal macrophages (MPM) were isolated from the peritoneal cavity of control E° mice, as well as from E° mice that consumed pomegranate juice (12.5 µL/mouse/day, equivalent to 0.35 µmoles of total polyphenols) for a period of two months. FIG. 12 shows the effect of pomegranate juice consumption by E° mice on their peritoneal macrophage lipids peroxidation and their ability to oxidize LDL. In FIG. 12(A), macrophage lipid peroxidation: Lipid peroxides content was assayed in cell sonicate of the MPM. FIG. 12(B) shows macrophage-mediated oxidation of LDL. In (B), MPM were incubated for six hours at 37° C. with LDL (100 ptg protein/mL), in the presence of 2 µmol/L of $CUSO_4$. At the end of the incubation, LDL oxidation was measured directly in the medium by the TBARS assay. FIG. 12(C) shows macrophage superoxide anion release. In (C), cells were stimulated by the addition of LDL (100 g protein/mL) and $CuSO_4$ (5 µmol/L) to MPM for one hour at 37° C. The amount of superoxide release was measured as described under "Methods". FIG. 12(D) shows macrophage total glutathione content. In (D), cell sonicate was used for this assay as described in "Methods". Results are given as mean±S.D. (n=3), * $p<0.01$ (vs. Control). PJ, Pomegranate juice.

FIG. 12A demonstrates that MPM isolated from juice after consumption of pomegranate juice contained 53% less lipid peroxides, in comparison to MPM from control E° mice. Incubation of these cells with LDL (100 µg of protein/mL) for 18 hours, under oxidative stress (in the presence of 2 µmol/L of $CuSO_4$), revealed that pomegranate juice consumption resulted in a 82% inhibition in macrophage-mediated oxidation of LDL, as measured by the TBARS assay (FIG. 12B).

Macrophage-mediated oxidation of LDL was shown to involve activation of NADPH oxidase and superoxide anion release (12), and it depends on the balance between cellular oxidants and antioxidants, including the glutathione system (13, 47).

FIG. 12C indeed shows that pomegranate juice consumption significantly reduced (by 49%) superoxide anion release from macrophages that were activated by incubation with LDL in the presence of copper ion. In parallel, the cellular content of glutathione increased by 25% in macrophages derived from E° mice that consumed pomegranate juice, in comparison to MPM from control E° mice (FIG. 12D).

B. Macrophage uptake of oxidized LDL and native LDL

Figure 13:
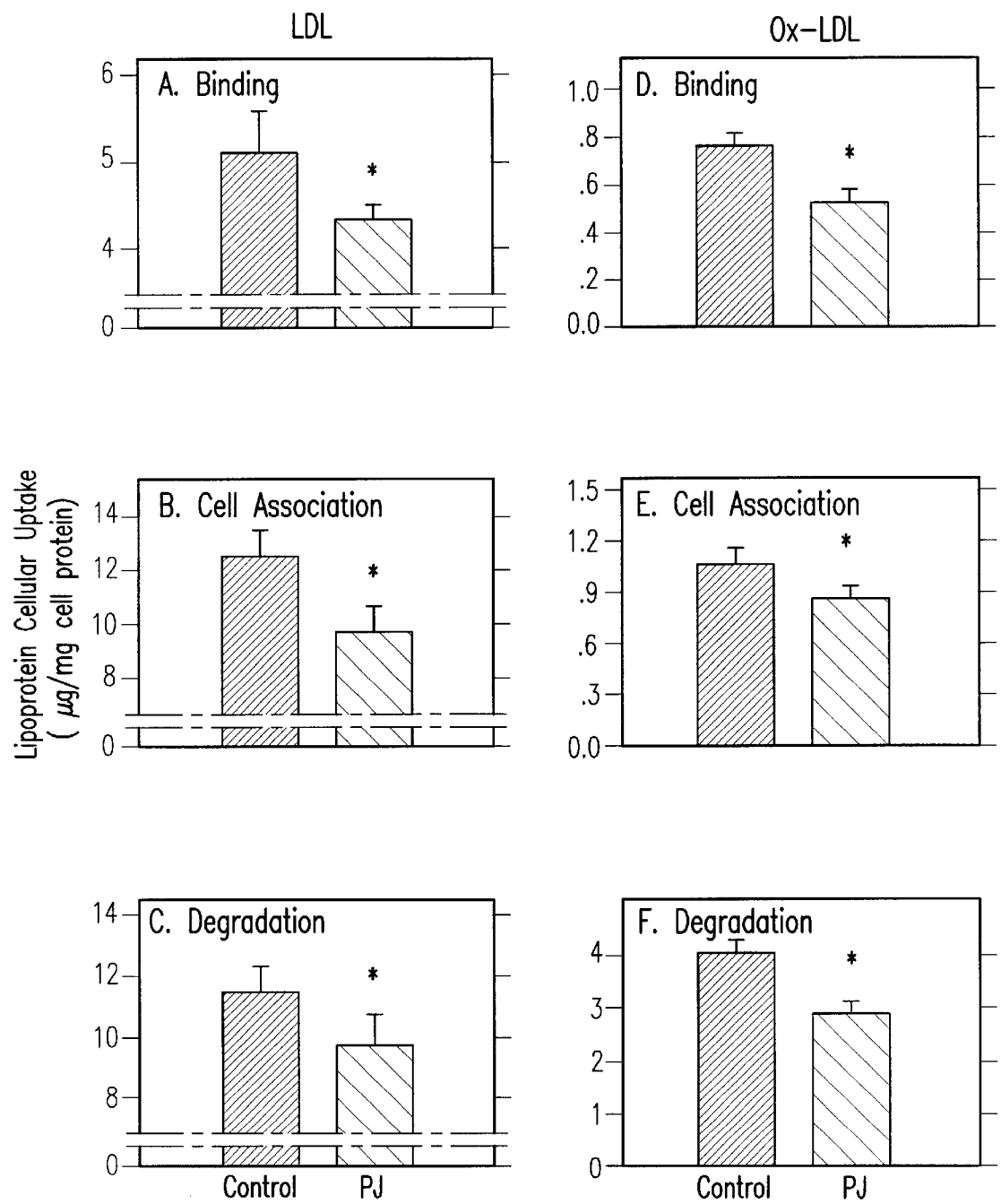
FIG. 13 shows the effect of pomegranate juice consumption by E° mice on their macrophage uptake of native or oxidized LDL.

The present invention also studied the effect of pomegranate juice consumption on macrophage uptake of oxidized-LDL (Ox-LDL) and native LDL. FIG. 13 shows the effect of pomegranate juice consumption by E° mice on their macrophage uptake of native or oxidized LDL. Mouse peritoneal macrophages (MPM) were isolated from the peritoneal fluid of control E° mice and E° mice that consumed 12.5 µL of pomegranate juice (PJ) for a period of two months. MPM were incubated with 10 µg of $^{125}$I-Ox-LDL or $^{125}$-LDL (10 µg of protein/mL) at 4° C. for two hours, followed by determination of lipoprotein binding (A, D), or at 37° C. for five hours for determination of lipoprotein cell-association (B, E) or lipoprotein degradation (C, F). Results are given as mean±S.D. (n=3), * $p<0.01$ (vs. Control). PJ, pomegranate juice.

Incubation of MPM, derived from E° mice that consumed 12.5 µL of pomegranate juice/mouse/day for a period of two months, with $^{125}$I-labeled oxidized LDL (10 µg of protein/ml) resulted in a significant reduction in cellular lipoprotein binding (FIG. 13A), cell-association (FIG. 13B) and degradation (FIG. 13C) by 16%, 22% and 15%, respectively, in comparison to Ox-LDL binding, cell-association and degradation by MPM from control E° mice. Similarly, pomegranate juice consumption also reduced macrophage binding, cell-association and degradation of native LDL by 31%, 19% and by 27%, respectively (FIGS. 13D, E, F).

IV. Platelet aggregation

Circulating human platelets play an important role in the development of atherosclerosis, and increased platelet aggregation is associated with enhanced atherogenicity (6–8). To study whether pomegranate juice can inhibit platelet aggregation, platelet rich plasma (PRP) was incubated for 30 minutes at 37° C. with increasing concentrations of pomegranate juice, after which aggregation was induced by the addition of collagen (2 µg/mL). A pomegranate juice dose-dependent inhibition, by up to 90%, of collagen-induced platelet aggregation was observed (FIG. 14A).

Analysis of PRP aggregation was also studied ex vivo. Following two weeks of pomegranate juice consumption, a significant ($p<0.02$) 11% reduction in collagen-induced platelet aggregation was noted, in comparison to platelet aggregation prior to PJ consumption at the beginning of the study (FIG. 14B).

Figure 14:
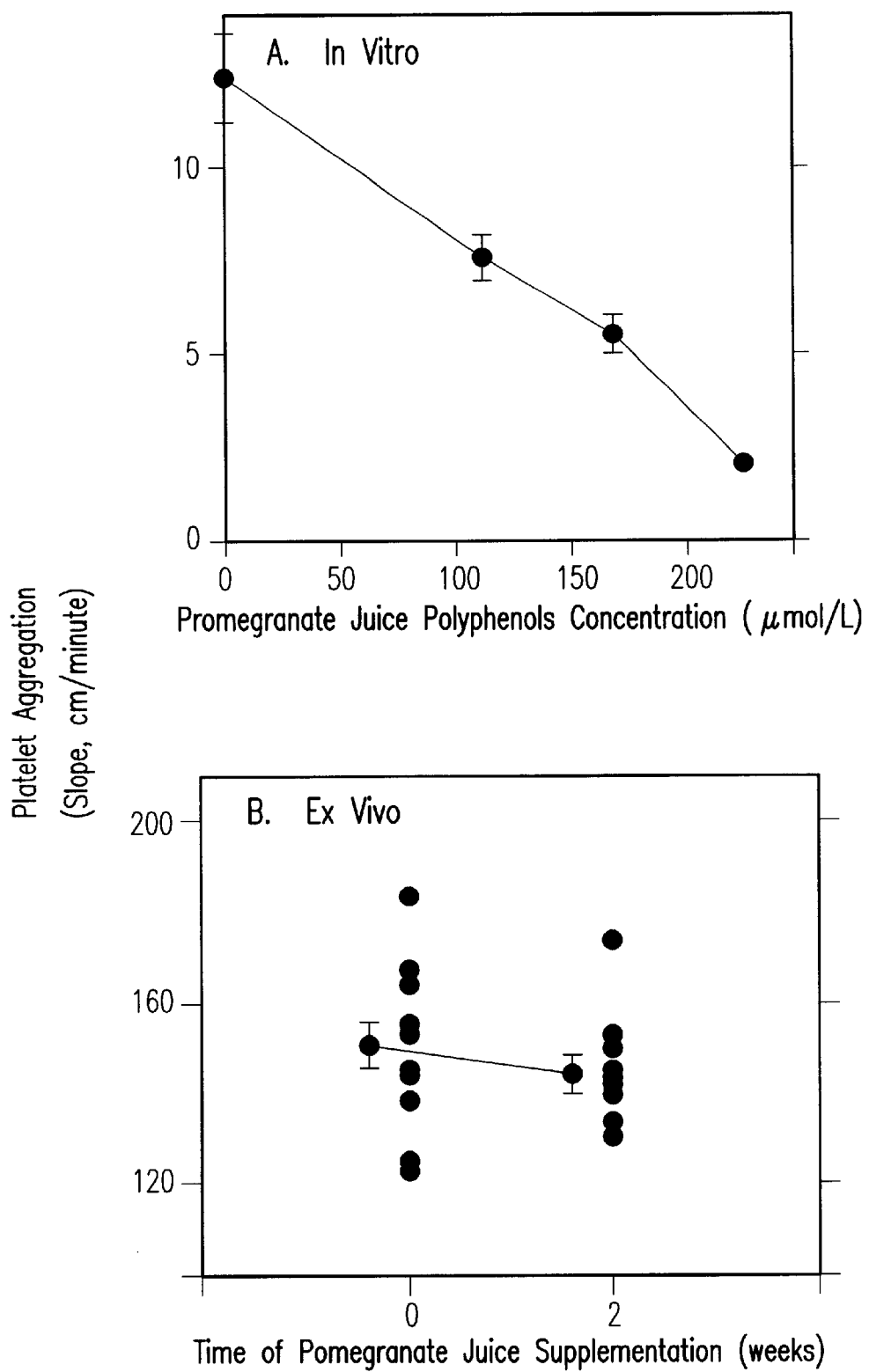
FIG. 14 shows the effect of pomegranate juice on human platelet aggregation in in vitro and ex-vivo studies.

FIG. 14 shows the effect of pomegranate juice on human platelet aggregation in both in vitro and ex-vivo studies. In FIG. 14(A), platelet-rich plasma (PRP) was incubated with increasing concentrations of pomegranate juice (0–220 µmol of polyphenols/L) for 10 minutes at 37° C., prior to analysis of platelet aggregation in response to 2 µg/mL of collagen. The extent of platelets aggregation is expressed as the slope (cm/min) of the aggregation curve. In FIG. 14(B), PRP was prepared from 11 healthy volunteers before (0) or after two weeks of pomegranate juice supplementation. Results are given for each individual and also as mean±S.D. (n=11).

SUMMARY DISCUSSION

The present invention analyzed the effect of pomegranate juice (PJ) on lipoprotein oxidation, aggregation and retention; on macrophage atherogenicity and on platelet aggregation in vitro and ex vivo in healthy male volunteers and in the atherosclerotic apolipoprotein E deficient (E°) mice. The in vitro studies demonstrated a significant dose-dependent antioxidant capability of PJ against lipid peroxidation in plasma (by up to 33%), in low density lipoprotein (LDL, by up to 43%), and in high density lipoprotein (HDL, by up to 22%). The water soluble fractions of pomegranate's inner and outer peels, but not the seeds, were even stronger antioxidants against LDL oxidation than the juice. The antioxidative effects of PJ against lipid peroxidation in whole plasma and in isolated lipoproteins were clearly shown, ex vivo, in humans and in the atherosclerotic mice following consumption of PJ for up to 2 and 14 weeks, respectively. The mechanisms for the antioxidative effects of PJ against lipid peroxidation could be related to its capacity to scavenge free radicals. Furthermore, PJ consumption by humans increased the activity of serum paraoxonase, which is an HDL-associated esterase that acts as a potent protector against lipid peroxidation.

Pomegranate juice not only inhibited LDL oxidation but also reduced two other related modifications of the lipoprotein, i.e., its retention to proteoglycan (as analyzed by LDL binding to chondroitin sulfate) and its susceptibility to aggregation (induced by LDL vortexing).

Macrophage atherogenicity was studied in mouse peritoneal macrophages (MPMs) from E° mice. Following PJ consumption, macrophage-mediated oxidation of LDL was reduced by 88% and this effect was associated with reduced cellular lipid peroxidation, reduced superoxide anion release and elevated content of macrophage glutathione. Furthermore, the uptake of oxidized LDL and that of native LDL, by MPMs that were obtained after PJ administration, were significantly reduced by about 20%. The above inhibitory effects of PJ consumption on the macrophage ability to oxidize LDL, from one hand, and on the uptake of oxidized LDL, from the other hand, can substantially contribute to attenuation of cellular cholesterol accumulation and foam cell formation.

Finally, PJ consumption by humans significantly inhibited, by up to 11%, their blood platelet aggregation, induced by collagen.

Taken together, the results of the present study clearly demonstrated a potent antiatherogenicity of pomegranate juice consumption in healthy humans and in atherosclerotic mice, and these characteristics could be associated mainly with PJ antioxidative properties.

The lipid peroxidation hypothesis of atherosclerosis (1–3) is supported by evidence for the occurrence of oxidized lipoproteins in the atherosclerotic lesion (54), by the increased oxidizability of LDL from atherosclerotic patients (55) and by the antiatherogenicity of some antioxidants against LDL oxidation (13, 56). The impressive ability of pomegranate extract to to inhibit in vitro and ex vivo lipid peroxidation in plasma, as well as in isolated LDL and HDL, was shown in several different oxidative systems including transition metal ions, free radical generator and arterial cells. By more than one assay (TBARS, lipid peroxides and conjugated dienes formation) the present invention was able to demonstrate the substantial antioxidative capacity of pomegranate to scavenge free radicals, a major mechanism for the action of some potent natural antioxidants, including vitamin E and flavonoids (57, 58). Pomegranate juice is rich in specific polyphenolic flavonoids, such as anthocyanines, which possess potent free radical scavenging capabilities.

While not wanting to be bound by the theory, it is believed that chelation of copper ion, in contrast, was probably not related to the inhibitory effect of pomegranate extract on LDL oxidation, as relatively high concentrations of copper ion did not overcome the inhibition of LDL oxidation by pomegranate juice. Similarly, other polyphenols-rich nutrients, such as licorice (24), were also not able to chelate copper ions.

It is worth noting that in the present study the inhibitory effect of pomegranate juice against LDL oxidation was shared also by aqueous extracts obtained from the outer and inner peels of pomegranates. When compared per total polyphenols content (or per weight), the peels were more potent antioxidants against LDL oxidation than the juice. These fractions may contain different flavonoid compositions from that present in the pomegranate juice, with a more potent antioxidative capacity.

Paraoxonase is an HDL-associated esterase, which was shown to protect the HDL, as well as LDL, from oxidation. This protection is probably the result of paraoxonase ability to hydrolyze specific oxidized lipids in oxidized lipoproteins (59, 60). The present invention demonstrated that pomegranate juice significantly increased serum arylesterase activity (a major activity of the enzyme paraoxonase), as demonstrated both in vitro (during plasma lipid peroxidation) and ex vivo in the human study. Paraoxonase is inactivated by lipid peroxides (61), and it has been recently demonstrated the ability of red wine flavonoids (23) and that of licorice derived glabridin (61) to preserve paraoxonase activity during lipoprotein oxidation. The present invention, however, showed not only preservation but also enhancement of paraoxonase activity.

While not wanting to be bound by the theory, it is believed that this latter effect may be partly related to the presence of calcium ion in PJ (29), as this ion is a co-factor for the enzyme arylesterase activity (36). The elevation in serum paraoxonase activity after pomegranate extract consumption was associated with increased plasma antioxidant status and with reduction in plasma oxidation. Furthermore, the susceptibility of HDL (the carrier of paraoxonase in serum) to oxidation was significantly reduced following PJ consumption. These results further strengthen the inverse association between serum paraoxonase activity and lipid peroxidation (59).

In the atherosclerotic, apolipoprotein E deficient (E°) mice, which are under oxidative stress (62), upon pomegranate juice consumption, a substantial reduction in the plasma lipid peroxidation state, as well as in the susceptibility of their LDL to copper ions-induced oxidation, was shown. These inhibitory effects were higher in the atherosclerotic mice than the effects shown in healthy human volunteers. This phenomenon may be related to the high initial oxidative stress, which exists in E° mice, that was substantially reduced by the pomegranate juice antioxidant capability.

Atherosclerosis is a multifactorial disease, and factors other than LDL oxidation can accelerate atherogenesis independently, or in association with lipid peroxidation. Such factors include LDL retention (5) and LDL aggregation (3).

LDL oxidation is thought to occur in the arterial wall after lipoprotein binding to extracellular matrix proteoglycans. The present invention has developed a simple assay to determine LDL binding to chondroitin sulfate as an indicator for "LDL retention." While in vitro, an impressive inhibitory effect of PJ on "LDL retention" could be observed; the ex vivo study revealed that in only 50–60% of the volunteers inhibition of "LDL retention" was achieved. This may be related to additional factors that affect "LDL retention" in vivo, such as the LDL density, charge, and its sialic acid content (63, 64).

LDL retention can predispose the lipoprotein to oxidation, and LDL oxidation can lead to an additional atherogenic modification-lipoprotein aggregation (21). Aggregated LDL is taken up by macrophages at an enhanced rate, leading to cellular cholesterol accumulation and foam cell formation (4).

Macrophages can also cause LDL aggregation, independently of its oxidation, following the secretion of proteoglycans from the cells under certain conditions (65). The present invention demonstrated that LDL aggregation was also inhibited in vitro by PJ and this may be related to hydrophobic interactions between PJ constituents and the lipoprotein (66). In the human study, however, in only 54% of the volunteers was LDL aggregation inhibited after PJ consumption. The inability of PJ to affect LDL aggregation ex vivo in all subjects may be related to LDL composition differences or dose and duration of administration. Such differences can affect LDL interaction with PJ constituents and, hence, can change lipoprotein-lipoprotein association (64) and LDL susceptibility to oxidation, which can then also affect lipoprotein aggregation. The observation that some subjects were refractory to LDL modifications may be related to the short time of pomegranate juice consumption.

Arterial wall macrophages play a major role during early atherogenesis. The present invention has demonstrated that, under oxidative stress, lipid peroxidation affects not only lipoproteins but also cellular lipids (52). Furthermore, cell-mediated oxidation of LDL can be achieved following incubation of lipid peroxidized macrophages with LDL, even in the absence of transition metal ion (52, 53). Macrophage-mediated oxidation of LDL is associated with activation of cellular NADPH oxidase which produces superoxide anions (12). Superoxide ions can be converted under certain conditions into a more potent reactive oxygen species (67), which can then convert native LDL to atherogenic oxidized LDL. Macrophage-mediated oxidation of LDL is substantially increased in glutathione-depleted cells and cellular lipid peroxides are formed under these conditions (13, 47).

The present study clearly showed that macrophage-mediated oxidation of LDL was substantially reduced by macrophages derived from E° mice after PJ consumption. This anti-atherogenic effect was associated with increased cellular glutathione content, reduced macrophage superoxide anion release and reduced macrophage lipid peroxidation. These observations further support a key role for cellular lipid peroxidation in macrophage-mediated oxidation of LDL (52, 53).

Polyphenolic flavonoids, which can accumulate in the cell plasma membrane and in the cytosol, as well as other constituents of pomegranate extract, can affect not only cellular oxygenases, such as NADPH oxidase (12) and macrophage antioxidants (such as the glutathione system (46)), but they can also cause conformational changes in plasma membrane constituents, such as cellular receptors for lipoproteins. The present invention thus analyzed the uptake of oxidized LDL, as well as native LDL, by peritoneal macrophages from E° mice, following PJ consumption. The present invention was able to demonstrate reduced cellular degradation, cell-association and cellular binding of both lipoproteins, in comparison to their interaction with cells from control mice. These results suggest that PJ constituents, which probably accumulate in the macrophage plasma membrane, may affect cellular receptors for lipoproteins by a stearic modification. It may be also that PJ constituents which accumulate intracellularly can affect lipoprotein receptors synthesis. Consumption of pomegranate juice by the atherosclerotic E° mice thus reduced oxidative stress in the cells (which was associated with reduced cell-mediated oxidation of LDL), and also reduced the uptake of oxidized LDL. Both of these processes contribute to attenuation of macrophage cholesterol accumulation and foam cell formation.

Finally, platelet activation, an additional risk factor for atherosclerosis (6), is also associated with oxidative stress (7). The ability of PJ consumption to reduce platelet activation in humans was supported by a direct effect of PJ on platelet aggregation as shown in vitro. This effect may be related to an interaction of PJ constituents with the platelet surface binding sites for collagen. It may also be that the antioxidative properties of PJ constituents, as demonstrated by their ability to scavenge free radicals, can attenuate oxidative stress-induced platelet activation.

In summary, the present invention was able to demonstrate impressive antiatherogenic capabilities of pomegranate juice or pomegranate extract in three related components of atherosclerosis, plasma lipoproteins, arterial macrophages and blood platelets. While not wanting to be bound by the theory, it is believed that the potent antioxidative capacity of pomegranate extract against lipid peroxidation may be the central link for the anti-atherogenic effects of pomegranate juice on lipoproteins, macrophages and platelets.

The present invention may be embodied in other specific forms without departing from its essential characteristics. The described embodiment is to be considered in all respects only as illustrative and not as restrictive. The scope of the invention is, therefore, indicated by the appended claims rather than by the foregoing description. All changes which come within the meaning and range of the equivalence of the claims are to be embraced within their scope.

REFERENCES

1) Aviram M. Beyond cholesterol: modifications of lipoproteins and increased atherogenicity. In: Atherosclerosis, Inflammation and Thrombosis. (G. G. Neri Semeri, G. F. Gensini, R. Abbate and D. Prisco., eds.). Scientific Press-Florence, Italy. pp. 15–36.(1993).
2) Witztum J. L. and Steinberg D. Role of oxidized low density lipoprotein in atherogenesis. *J. Clin. Invest.* 88: 1785–1792 (1991).
3) Aviram M. Modified forms of low density lipoprotein and atherosclerosis. *Atherosclerosis* 98: 1–9 (1993).
4) Suits A. G, Chait A, Aviram M, Heinecke J. W. Phagocytosis of aggregated lipoprotein receptor-dependent foam-cell formation. *Proc. Natl. Acad. Sci. U.S.A.* 86: 2713–2717 (1989).
5) Williams K. J. and Tabas I. The response-to-retention hypothesis of early atheogenesis. *Arterioscler. Thromb. Vasc. Biol.* 15: 551–561 (1995).
6) Aviram M. Platelets and arterial wall lesion In: Curr. Opin. Lipidol. Atherosclerosis: cell biology and lipoproteins. Coetzee G. A. and van der Westhuyzen D. R. (Eds.) 3: 344–348 (1992).
7) Aviram M. LDL-platelet interaction under oxidative stress induces macrophage foam cell formation. *Thromb. Haemost.* 74: 560–564 (1995).
8) Sinzinger H. Role of platelets in atherosclerosis. *Semin. Thromb. Hemost.* 12: 124–133 (1986).
9) Parthasarathy S., Printz D. J., Boyd D., Joy L., and Steinberg D. Macrophage oxidation of low-density lipoprotein generates a modified form recognized by the scavenger receptor. *Arteriosclerosis* 6: 505–510 (1986).
10) Berliner J. A., Navab M., Fogelman A. M., Frank J. S., Demer L. L., Edwards P. A., Watson A. D., Lusis A. J. Atherosclerosis: basic mechanisms. Oxidation, inflammation, and genetics. *Circulation* 91:2488–2496 (1995).
11) Steinbrecher U. P., Parthasarathy S., Leake D. S., Witztum J. L., Steinberg D. Modification of low density lipoprotein by endothelial cells involves lipid peroxidation and degradation of low density lipoprotein phospholipids. *Proc. Natl. Acad. Sci. USA*. 81: 3883–3887 (1984).
12) Aviram M., Rosenblat M., Etzioni A. and Levy R. Activation of NADPH oxidase is required for macrophage-mediated oxidation of low-density lipoprotein. *Metabolism* 45: 1069–1079 (1996).
13) Aviram M. and Fuhrman B. LDL oxidation by arterial wall macrophages depends on the oxidative status in the lipoprotein and in the cells: role of prooxidants vs. antioxidants. *Mol. Cell. Biochem.* 188:149–159 (1998).

14) Parthasarathy S., Yang S. G., Witztum J. L., Pittman R. C. and Steinberg D. Probucol inhibits oxidative modification of low density lipoprotein. *J. Clin. Invest.* 77: 641–644 (1986).
15) Pentikainen M. O., Lindstedt K. A. and Kovanen P. T. Inhibition of the oxidative modification of LDL by Nitecapone. *Arterioscler. Thromb. Vasc. Biol.* 15: 740–747 (1995).
16) Breugnot C., Lliou J. P., Privat S., Robin F., Village J. P. and Lenaers A. In vitro and ex vivo inhibition of the modification of low-density lipoprotein by indapamide. *J. Cardiovasc. Pharmacol.* 20: 340–347 (1992).
17) Parthasarathy R., Morales A. J. and Murphy A. A. Antioxidant: a new role for RU-486 and related compounds. *J. Clin. Invest.* 1990–1995 (1994).
18) Lavy A., Ben Amotz A. and Aviram M. Preferential inhibition of LDL oxidation by the all-trans isomer of β-carotene in comparison to the 9-cis β-carotene. *Eur, J. Clin, Chem. Clin. Biochem.* 31: 83–90 (1993).
19) Levy Y., Ben-Amtotz A. and Aviram M. Effect of dietary supplementation of different β-carotene isomers on lipoprotein oxidative modification. *J. Nutr. Environ. Med.* 5: 13–22 (1995).
20) Fuhrman B., Ben-Yaish L., Attias J., Hayek T. and Aviram M. Tomato lycopene and β-carotene inhibit low density lipoprotein oxidation and this effect depends on the lipoprotein vitamin E content. *Nutr. Metab. Cardiovasc. Dis.* 7: 433–443 (1997).
21) Maor I., Hayek T., Coleman R. and Aviram M. Plasma LDL oxidation leads to its aggregation in the atherosclerotic apolipoprotein E deficient mice. *Arterioscler. Thromb. Vasc. Biol.* 17:2995–3005 (1997).
22) Fuhrman B., Lavy A. and Aviram M. Consumption of red wine with meals reduces the susceptibility of human plasma and low density lipoprotein to undergo lipid peroxidation. *Am. J. Clin. Nutr.* 61: 549–554 (1995).
23) Hayek T., Fuhrman B., Vaya J., Rosenblat M., Belinki P., Coleman R., Elis A. and Aviram M. Reduced progression of atherosclerosis in the apolipoprotein E deficient mice following consumption of red wine, or or its polyphenols quercetin, or catechin, is associated with reduced susceptibility of LDL to oxidation and to aggregation. *Arterioscler. Thromb. Vasc. Biol.* 17:2744–2752 (1997).
24) Fuhrman B., Buch S., Vaya J., Belinki P. A., Coleman R., Hayek T. and Aviram M. Licorice extract and its major polyphenol glabridin protect low density lipoprotein against lipid peroxidation; in vitro and ex-vivo studies in humans and in atherosclerotic apolipoprotein E-deficient mice. *Am. J. Clin. Nutr.* 66: 267–275 (1997).
25) Aviram M. and Kassem E. Dietary olive oil reduces the susceptibility of low density lipoprotein to lipid peroxidation and inhibits lipoprotein uptake by macrophages. *Ann. Nutr. Metab.* 37: 75–84 (1993).
26) eftaman E. and Bennett S. T. Identification of estrone in pomegranate seeds. *Phytochemistry* 5: 1337–1339 (1966).
27) Moneam N. M. A., El Sharasky A. S., Badreldin M. M. Oestrogen content of pomegranate seeds. *J. Chromatogr.* 438: 438–442 (1988).
28) Sharaf A. and Nigm S. A. R. The oestrogenic acitvity of pomegranate seed oil. *J. Endocrinol.* 29:91–92(1964).
29) Cemeroglu B., Artik N., Erbas S. Extraction and composition of pomegranate juice. *Fluessiges Obst.* 59:335–340 (1992).
30) El-Nemr S. E., Ismail I. A., Ragab M. Chemical composition of juice and seeds of pomegranate fruit. *Nahrung* 34: 601–606 (1990).
31) Narr Ben C., Ayed N., Metche M. Quantitative determination of the polyphenolic content of pomegranate peel. *Z. Lebensm. Unters. Forsch.* 203: 374–378 (1996).
32) U.S. Pat. No. 5,411,733.
33) Plump A. S., Smith J. D., Hayek T. et al. Severe hypercholesterolemia and atherosclerosis in apolipoprotein E-deficient mice created by homologous recombination in ES cells. *Cell* 71: 343–353 (1992).
34) Buege J. A., Aust S. D. Microsomal lipid peroxidation. *Methods Enzymol.* 52: 302–310 (1978).
35) El-Saadani., Esterbauer N., El-Sayed M., Goher M., Nasear A. Y., Jurgens G. A sepctrophotometric assay for lipid peroxides in serum lipoproteins using a commercially available reagent. *J. Lipid. Res.* 30: 627–630 (1989).
36) Gan K. N., Smolen A., Eckerson H. W., and La Du B. N. Purification of human serum paraoxonase/arylesterase. Evidence for one esterase catalyzing both activities. *Drug. Metab. Dispos.* 19: 100–106 (1991).
37) Miller N. J., Rice-Evans C., Davies M. J., Gopinathan V. and Milner A. A novel method for measuring antioxidant capacity and its application to monitoring the antioxidant status in premature neonates. *Clinical Science* 84: 407–412 (1993).
38) Aviram M. Plasma lipoprotein separation by discontinuous density gradient ultracentrifugation in hyperlipoproteinemic patients. *Biochem. Med.* 30: 111–118 (1983).
39) Lowry O. H., Rosebrough N. J., Farr L., Randall R. J. Protein measurement with the Folin phenol reagent. *J. Biol. Chem.* 193: 265–275 (1951).
40) Esterbauer H., Strigel G., Puhl H., Rothender M. Continuous monitoring of in vitro oxidation of human low density lipoprotein. *Free. Radic. Res. Commun.* 6: 67–75 (1989).
41) Khoo J. C., Miller E., McLoughlin P., Steinberg D. Enhanced macrophage uptake of low density lipoprotein after self-aggregation. *Arteriosclrosis* 8: 348–358 (1988).
42) Assman G., Schriewer H., Schmitz G., Hagele E. O. Quantification of high-density-lipoprotein cholesterol by preicipitation with phosphotungstic acid-$MgCl_2$. *Clin. Chem.* 29: 2026 (1983).
43) Van de Lest C. H., Versteeg E. M., Veerkamp J. H., van Kuppevelt T. H. A. Spectrophotometric method for the determination of heparan sulfate. *Biochim. Biophys. Acta.* 1994; 1201: 305–311.
44) Aviram M., Willams K. J., McIntosh. R. A., Carpentier Y. A., Tall A. R., to Deckelbaum R. J. Intralipid infusion abolishes ability of human serum to cholesterol-load cultured macrophages. *Arteriosclerosis* 9: 67–75 (1989).
45) Tietze F. Enzymatic method for quantitative determination of nanogram amounts of total and oxidized glutathione;application to mammalian blood and other tissues. *Anal. Biochem.* 27: 502–522 (1969).
46) Johnston R. B, Keele B. B., Jr. : Mirsa H. P., Lehmeyer J. E., Webb L. S., Bachner R. L., RaJagopalan K. V. The role of superoxide anion generation in phagocytic bactericidal activity. *J. Clin. Invest.* 55: 1357 (1975).
47) Rosenblat M. and Aviram M. Macrophage glutathione content and glutathione and glutathione peroxidase activity are inversely related to cell-mediated oxidation of LDL. *Free. Radic. Biol. Med.* 24: 305–317 (1997).
48) Bilheimer D. W., Eisenberg S. and Levy R. I. The metabolism of very low density lipoprotein proteins. 1. Preliminary in vitro and in vivo observations. *Biochim. Biophys. Acta.* 260: 212–221 (1972).
49) Bierman E. L., Stein 0. and Stein Y. Lipoprotein uptake and metabolism by rat aortic smooth muscle cells in tissue culture. *Circ. Res.* 35: 136–150 (1974).
50) Hussein O., Rosenblat M., Schlezinger S., Keidar S., Aviram M. Reduced platelet aggregation after fluvastatin therapy is associated with altered platelet lipid composition and drug binding to the platelets. Br. J. Clin. Pharmacol. 44: 77-84 (1997).

51) Blois M. S. Antioxidant determination by the use of a stable free radical, *Nature* 181: 1199–1200 (1958).
52) Fuhrman B., Oiknine J. and Aviram M. Iron induces lipid peroxidation in cultured macrophages increases their ability to oxidatively modify LDL and afect their secretory properties. *Atherosclerosis* 111: 65–78 (1984).
53) Fuhrman B., Oiknine J., Keidar S., Ben-Yaish L., Kaplan M. and Aviram M. Increased uptake of LDL by oxidized macrophages is the results of an initial enhanced LDL receptor activity and of a further progressive oxidation of LDL. *Free. Radic. Biol. Med.* 23: 34–46 (1997).
54) Aviram M., Maor I., Keidar S., Hayek T., Oiknine J., Bar-El Y., Adler Z., Kertzman V., Milo S. Lesioned low density lipoprotein in atherosclerotic apolipoprotein E-deficient transgenic mice and in humans is oxidized and aggregated. *Biochem. Biophys. Res. Commun.* 216: 501–513 (1995).
55) Lavy A., Brook J. G., Dankner G., Ben Amotz A., Aviram M. Enahnced in vitro oxidation of plasma lipoproteins derived from hypercholeste-rolemic patients. *Metabolism* 40: 794–799(1991).
56) Aviram M. Oxidized low density lipoprotein (Ox-LDL) interaction with macrophages in atherosclerosis and the antiatherogenicity of antioxidants. *Eur. J. Clin. Chem. Clin. Biochem.* 34: 599–608 (1996).
57) Schwenke D. C., Behr S. R. Vitamin E combined with selenium inhibits atherosclerosis in hypercholesterolemic rabbits independently of effects on plasma cholesterol concentrations. *Circulation Res.* 83: 366–77 (1998).
58) Rice-Evans C. A., Miller N. J. and Paganga G. Structure-antioxidant activity relationships of flavonoids and phenolic acid. *Free. Radic. Biol. Med.* 20: 933–956 (1996).
59) Aviram M., Rosenblat M., Bisgaier C. L., Newton R. S., Primo-Parmo S. L., and La Du B. N. Paraoxonase inhibits high density lipoprotein (HDL) oxidation and preserves its functions: A possible peroxidative role for paraoxonase. *J. Clin. Invest.* 101: 1581–1590 (1998).
60) Navab M, Berliner J. A., Watson A. D., Hama S. Y., Territo M. C., Lusis A. J., Shih D. M., Van Lenten B. J., Frank J. S., Demer L. L., Edwards P. A., Fogelman A. M. The Yin and Yang of oxidation in the development of the fatty streak a review based on the 1994 George Lyman Duff Memorial Lecture. *Arterioscler. Thromb. Vasc. Biol.* 17: 831–842 (1996).
61) U.S. Pat. No. 5,840,308
62) Hayek T., Oiknine J., Brook J. G. and Aviram M. Increased plasma lipoprotein lipid peroxidation in apo E-deficient mice. *Biochem. Biophys. Res. Commun.* 201: 1567–1574 (1994).
63) Camejo G., Waich S., Mateu L., Acquatella H., LaLaguna F., Quintero G., Berrizbeitia M. L. Differences in the structure of plasma low density lipoproteins and their relationship to the extent of interaction with arterial wall components. *Ann. New. York. Acad. Sci.* 275: 153–168 (1976).
64) Camejo G., Lopez A., Lopez F., Quinones J. Interaction of low density lipoproteins with arterial proteoglycans: the role of charge and sialic acid content. *Atherosclerosis* 55: 93–105 (1985).
65) Maor I. and Aviram M. Macrophage released proteoglycans are involved in cell-mediated aggregation of LDL. *Atherosclerosis* 142: 57–66 (1998).
66) Khoo J. C., Miller E., McLoughlin P. and Steinberg D. Prevention of low density lipoprotein aggregation by high density lipoprotein or apolipoprotein A-I. *J. Lipid Res.* 31: 645–652 (1990).
67) Bedwell S., Dean R. T., Jessup W. The action of defined oxygen-centred free radicals on human low density lipoprotein. *Biochem. J.* 262: 707–712 (1989).

What is claimed is:

1. A composition, the biologically active component of the composition consisting essentially of an extract from pomegranate fruit, the composition further comprising a carrier, wherein the extract is prepared by a process comprising the steps of:

(a) crushing, squeezing, and enzymatically treating the whole fruits of pomegranate including inner and outer peels and the seeds to yield a juice component and an insoluble by-product component;

(b) separating the juice component from the insoluble by-product component;

(c) resuspending the insoluble by-product component in an aqueous medium;

(d) crushing, squeezing, and mixing the resuspended by-product component to yield a soluble portion and an insoluble portion;

(e) separating the soluble portion from the insoluble portion; and (f) combining the soluble portion with the juice component to produce the extract.

2. The composition of claim 1, wherein the composition is in a form selected from a group consisting of nutritional supplements, pharmaceutical preparations, vitamin supplements, food additives or foods supplements.

3. The composition of claim 2, wherein the composition is a pharmaceutical preparation, and the carrier is a pharmaceutically acceptable carrier.

4. The composition of claim 2, wherein the composition is in a form selected from a group consisting of nutritional supplements, vitamin supplements, food additives or foods supplements, and the carrier is a dietary suitable carrier.

5. The composition of claim 1, wherein the composition is in a dosage unit form selected from a group consisting of tablets, suspensions, implants, solutions, emulsions, capsules, powders, syrups, liquid compositions, ointments, lotions, creams, pastes, gels, and the like.

6. The composition of claim 1, wherein the extract is present in a dosage unit in an amount that contains at least 30 to 3000 $\mu$mols per dosage unit of polyphenols, wherein the polyphenol are those naturally present in the extract of pomegranate.

7. The composition of claim 1 further comprising a step of chilling whole fruits of pomegranate before the crushing and squeezing step.

8. The composition of claim 1 wherein in step (a), the whole fruit is enzymatically treated with pectinase.

9. An antioxidative composition for treating disorders associated with a condition selected from the group consisting of lipoprotein oxidation, lipoprotein aggregation, lipoprotein retention, macrophage atherogenicity, platelet activation, and atherosclerosis, the biologically active component of the composition consisting essentially of an extract from pomegranate fruit, wherein the extract is prepared by a process comprising the steps of:

(a) crushing, squeezing, and enzymatically treating the whole fruits of pomegranate including inner and outer peels and the seeds to yield a juice component and an insoluble by-product component;

(b) separating the juice component from the insoluble by-product component;

(c) resuspending the insoluble by-product component in an aqueous medium;

(d) crushing, squeezing, and mixing the resuspended by-product component to yield a soluble portion and an insoluble portion;

(e) separating the soluble portion from the insoluble portion; and (d) combining the soluble portion with the juice component to produce the extract.

10. The antioxidative composition of claim 9, wherein the composition is in a dosage unit form selected from a group consisting of tablets, suspensions, implants, solutions, emulsions, capsules, powders, syrups, liquid compositions, ointments, lotions, creams, pastes, gels, and the like.

11. The antioxidative composition of claim 9, wherein the extract is present in a dosage unit in an amount that contains at least 30 to 3000 $\mu$mols per dosage unit of polyphenols, wherein the polyphenols are those naturally present in the extract of pomegranate.

12. The antioxidative composition of claim 9, wherein the disorders are selected from a group consisting of arteriosclerotic heart disease and its associated complications (including myocardial infarction); cerebral vascular disease (including cerebral insufficiency or stroke); peripheral vascular disease (including peripheral vascular disease in the aorta and femoral and corotid arteries); abdominal aortic aneurysms; renal artery stenosis; arteriosclerotic disease, disorders associated with transplant complications; disorders associated with post-operative heart valve replacement; disorders associated with the complications of diabetes mellitus; thrombophlebitis; and other disorders associated with increased platelets and increased platelet activation.

13. The antioxidative composition of claim 9, wherein in step (a), the whole fruit is enzymatically treated with pectinase.

14. A composition, the biologically active component of the composition consisting essentially of an extract from pomegranate fruit, the composition further comprising a carrier, wherein the extract is prepared by a process comprising the steps of:

(a) crushing, squeezing, and enzymatically treating the whole fruits of pomegranate including inner and outer peels and the seeds to yield a juice component and an insoluble by-product component;

(b) separating the juice component from the insoluble by-product component;

(c) resuspending the insoluble by-product component in an aqueous medium;

(d) crushing, squeezing, and mixing the resuspended by-product component to yield a soluble portion and an insoluble portion; and (e) separating the soluble portion from the insoluble portion to produce the extract containing the soluble portion.

15. The composition of claim 14 further comprising a step of chilling whole fruits of pomegranate before the crushing and squeezing step.

16. The composition of claim 14 wherein in step (a), the whole fruit is enzymatically treated with pectinase.

17. An antioxidative composition for treating disorders associated with a condition selected from the group consisting of lipoprotein oxidation, lipoprotein aggregation, lipoprotein retention, macrophage atherogenicity, platelet activation, and atherosclerosis, the biologically active component of the composition consisting essentially of an extract from pomegranate fruit, wherein the extract is prepared by a process comprising the steps of:

(a) crushing, squeezing, and enzymatically treating the whole fruits of pomegranate including inner and outer peels and the seeds to yield a juice component and an insoluble by-product component;

(b) separating the juice component from the insoluble by-product component; (c) resuspending the insoluble by-product component in an aqueous medium;

(d) crushing, squeezing and mixing the resuspended by-product component to yield a soluble portion and an insoluble portion; and (e) separating the soluble portion from the insoluble portion to produce the extract containing the soluble portion.

18. The antioxidative composition of claim 17, wherein in step (a), the whole fruit is enzymatically treated with pectinase.

\* \* \* \* \*